(12) United States Patent
Jeppesen et al.

(10) Patent No.: US 6,525,086 B2
(45) Date of Patent: Feb. 25, 2003

(54) COMPOUNDS, THEIR PREPARATION AND USE

(75) Inventors: Lone Jeppesen, Virum (DK); Paul Stanley Bury, Kobenhavn (DK); Per Sauerberg, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/808,495

(22) Filed: Mar. 14, 2001

(65) Prior Publication Data

US 2001/0029256 A1 Oct. 11, 2001

Related U.S. Application Data

(62) Division of application No. 09/420,380, filed on Oct. 21, 1999, now Pat. No. 6,214,820.
(60) Provisional application No. 60/106,658, filed on Nov. 2, 1998.

(30) Foreign Application Priority Data

Nov. 2, 1998 (DK) .......................................... 1998 01357

(51) Int. Cl.[7] .................... C07D 405/12; C07D 407/12; C07D 409/12; A61K 31/38; A61K 31/335
(52) U.S. Cl. ....................... 514/431; 514/450; 514/320; 514/337; 514/342; 514/255; 514/256; 514/247; 514/252; 514/311; 514/307; 514/259; 514/249; 514/253; 514/266; 514/232.8; 514/241; 514/183; 514/402; 514/397; 514/406; 514/383; 514/372; 514/378; 514/374; 514/364; 514/361; 514/382; 514/414; 514/391; 514/422; 514/365; 549/12; 549/354; 548/364.4; 548/262.2; 548/206; 548/215; 548/240; 548/131; 548/127; 548/128; 548/134; 548/136; 548/250; 548/300.1; 548/311.4; 548/454; 548/465; 548/403; 548/122; 548/123; 548/124; 548/125; 548/143; 548/146; 546/202; 546/196; 546/269; 546/152; 546/148; 544/405; 544/333; 544/238; 544/283; 544/353; 544/257; 544/264; 544/145; 544/147; 544/180; 544/179; 544/359

(58) Field of Search .................... 514/183, 431, 514/397, 372, 364, 414, 365, 342, 247, 307, 53, 241; 549/9, 208, 12, 354

(56) References Cited

FOREIGN PATENT DOCUMENTS

| WO | WO 96/04260 | 2/1996 |
|---|---|---|
| WO | WO 96/04261 | 2/1996 |
| WO | WO 97/25042 | 7/1997 |
| WO | WO 97/36579 | 10/1997 |
| WO | WO 99/19313 | 4/1999 |

*Primary Examiner*—John M. Ford
(74) *Attorney, Agent, or Firm*—Cheryl H. Agris; Reza Green

(57) ABSTRACT

The present invention relates to compounds of formula (I)

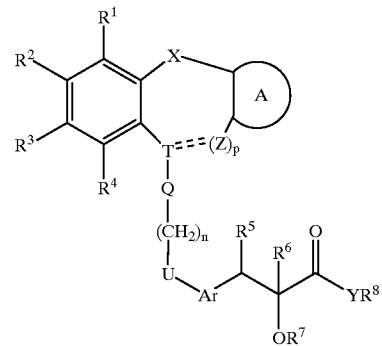

(Ia)

wherein $R^1$, $R^2$, $R^3$, $R^4$, $R^5$, $R^6$, $R^7$, $R^8$, A, X, T, Q, Z, U, Y, Ar, p and n are as defined in the specification. These compounds are useful in the treatment and/or prevention of conditions mediated by nuclear receptors, in particular the Peroxisome Proliferator-Activated Receptors (PPAR).

49 Claims, No Drawings

COMPOUNDS, THEIR PREPARATION AND USE

CROSS-REFERENCE TO RELATED APPLICATIONS

This application is a divisional of U.S. application Ser. No. 09/420,380 filed on Oct. 21, 1999, now U.S. Pat. No. 6,214,820, and claims priority under 35 U.S.C. 119 of Danish application no. PA 1998 01357 filed on Oct. 21, 1998 and U.S. provisional application No. 60/106,658 filed on Nov. 2, 1998, the contents of which are fully incorporated herein by reference.

FIELD OF INVENTION

The present invention relates to novel compounds, pharmaceutical compositions containing them, methods for preparing the compounds and their use as medicaments. More specifically, compounds of the invention can be utilized in the treatment of conditions mediated by nuclear receptors, in particular the Peroxisome Proliferator-Activated Receptors (PPAR). The present compounds reduce blood glucose and triglyceride levels and are accordingly useful for the treatment of ailments and disorders such as diabetes and obesity.

The present invention also relates to a process for the preparation of the above said novel compounds, their derivatives, their analogs, their tautomeric forms, their stereoisomers, their polymorphs, their pharmaceutically acceptable salts, pharmaceutically acceptable solvates and pharmaceutical compositions containing them.

The compounds are useful for the treatment and/or prophylaxis of insulin resistance (type 2 diabetes), impaired glucose tolerance, dyslipidemia, disorders related to Syndrome X such as hypertension, obesity, insulin resistance, hyperglycemia, atherosclerosis, hyperlipidemia, coronary artery disease and other cardiovascular disorders. The compounds of the present invention are also useful for the treatment of certain renal diseases including glomerulonephritis, glomerulosclerosis, nephrotic syndrome, hypertensive nephrosclerosis. These compounds may also be useful for improving cognitive functions in dementia, treating diabetic complications, psoriasis, polycystic ovarian syndrome (PCOS) and prevention and treatment of bone loss, e.g. osteoporosis.

BACKGROUND OF THE INVENTION

Coronary artery disease (CAD) is the major cause of death in type 2 diabetic and metabolic syndrome patients (i.e. patients that fall within the 'deadly quartet' category of impaired glucose tolerance, insulin resistance, hypertriglyceridemia and/or obesity).

The hypolipidemic fibrates and antidiabetic thiazolidinediones separately display moderately effective triglyceride-lowering activities although they are neither potent nor efficacious enough to be a single therapy of choice for the dyslipidemia often observed in type 2 diabetic or metabolic syndrome patients. The thiazolidinediones also potently lower circulating glucose levels of type 2 diabetic animal models and humans. However, the fibrate class of compounds are without beneficial effects on glycemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialized proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid b-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

A number of compounds have been reported to be useful in the treatment of hyperglycemia, hyperlipidemia and hypercholesterolemia (U.S. Pat. No. 5,306,726, PCT Publications nos. W091/19702, WO 95/03038, WO 96/04260, WO 94/13650, WO 94/01420, WO 97/36579, WO 97/25042, WO 95/17394, WO 99/08501, WO 99/19313 and WO 99/16758).

SUMMARY OF THE INVENTION

It seems more and more apparent that glucose lowering as a single approach does not overcome the macrovascular complications associated with type 2 diabetes and metabolic syndrome. Novel treatments of type 2 diabetes and metabolic syndrome must therefore aim at lowering both the overt hypertriglyceridaemia associated with these syndromes as well as alleviation of hyperglycemia.

The clinical activity of fibrates and thiazolidinediones indicates that research for compounds displaying combined PPAR α and PPAR γ activation should lead to the discovery of efficacious glucose and triglyceride lowering drugs that have great potential in the treatment of type 2 diabetes and the metabolic syndrome (i.e. impaired glucose tolerance, insulin resistance, hypertriglyceridemia and/or obesity).

DETAILED DESCRIPTION OF THE INVENTION

Accordingly, the present invention relates to compounds of formula (Ia):

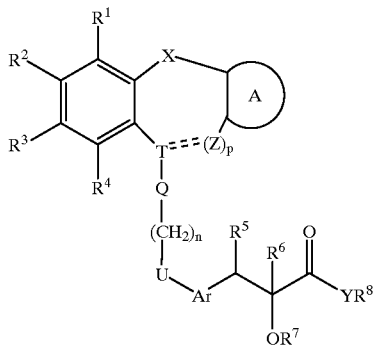

(Ia)

wherein $R^1$, $R^2$, $R^3$, and $R^4$ independently of each other represent hydrogen, halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein $R^{11}$ and $R^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano; or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl;

ring A represents a 5–6 membered cyclic ring, optionally substituted with one or more halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-12}$alkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{11}$, or —SO$_2$R$^{12}$, wherein $R^{11}$ and $R^{12}$ independently of each other are selected from hydroxy, halogen, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano;

X is a valence bond, —(CHR$^9$)—, —(CHR$^9$)—CH$_2$—, —CH═CH—, —O—, —O—(CHR$^9$)—, —S—(CHR$^9$)—, —(NR$^9$)—CH$_2$—, —(CHR$^9$)—CH═CH—, —(CHR$^9$)—CH$_2$—CH$_2$—, —(C═O)—, —O—CH$_2$—O—, —(NR$^9$)—, —(NR$^9$)—S(O$_2$)—, —CH═(CR$^9$)—, —(CO)—(CHR$^9$)—, —CH$_2$—(SO)—, —S—, —(SO)—, —(SO$_2$)—, —CH$_2$—(SO$_2$)—, —CH$_2$—O—CH$_2$—, wherein R$^9$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{13}$, or —SO$_2$R$^{14}$, wherein R$^{13}$ and R$^{14}$ independently of each other are selected from hydroxy, halogen, $C_{1-6}$alkoxy, amino optionally substituted with one or more $C_{1-6}$alkyl, perhalomethyl or aryl;

T is >N—, >CH—, >C<, —CH$_2$—N<;

Z is —CH$_2$—, ═CH—, >N—, —O—, —S—, >CO, >SO, >SO$_2$, >NR$^{15}$, wherein R$^{15}$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{16}$, or —SO$_2$R$^{17}$, wherein R$^{16}$ and R$^{17}$ independently of each other are selected from hydroxy, halogen, $C_{1-6}$alkoxy, amino optionally substituted with one or more $C_{1-6}$alkyl, perhalomethyl or aryl;

Q is —O—, —S—, >NR$^{18}$, wherein R$^{18}$ is hydrogen, halogen, hydroxy, nitro, cyano, formyl, $C_{1-12}$alkyl, $C_{1-12}$alkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, $C_{1-12}$alkylamino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —COR$^{19}$, or —SO$_2$R$^{20}$, wherein R$^{19}$ and R$^{20}$ independently of each other are selected from hydroxy, halogen, $C_{1-6}$alkoxy, amino optionally substituted with one or more $C_{1-6}$alkyl, perhalomethyl or aryl;

U is —O—, —S—, >SO$_2$, >NR$^{21}$, wherein R$^{21}$ is hydrogen or $C_{1-6}$alkyl;

T══(Z)$_p$ represents a single bond or a double bond;

Ar represents arylene, heteroarylene, or a divalent heterocyclic group optionally substituted with one or more $C_{1-6}$alkyl or aryl;

$R^5$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl or aralkyl; optionally substituted with one or more halogen, perhalomethyl, hydroxy, nitro or cyano; or $R^5$ forms a bond together with $R^6$;

$R^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl, acyl or aralkyl; optionally substituted with one or more halogen, perhalomethyl, hydroxy, nitro or cyano; or $R^6$ forms a bond together with $R^5$;

$R^7$ represents hydrogen, $C_{1-12}$alkyl, $C_{4-12}$-alkenynyl, $C_{2-12}$-alkenyl, $C_{2-12}$-alkynyl, aryl, aralkyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, acyl, heterocyclyl, heteroaryl or heteroaralkyl groups; optionally substituted with one or more halogen, perhalomethyl, hydroxy, nitro or cyano;

$R^8$ represents hydrogen, $C_{1-12}$alkyl, $C_{4-12}$-alkenynyl, $C_{2-12}$-alkenyl, $C_{2-12}$-alkynyl, aryl, aralkyl, heterocyclyl, heteroaryl or heteroaralkyl groups; optionally substituted with one or more halogen, perhalomethyl, hydroxy, nitro or cyano;

Y represents oxygen, sulphur or $NR^{10}$, where $R^{10}$ represents hydrogen, $C_{1-12}$alkyl, aryl, hydroxy$C_{1-12}$alkyl or aralkyl groups or when Y is $NR^{10}$, $R^8$ and $R^{10}$ may form a 5 or 6 membered nitrogen containing ring, optionally substituted with one or more $C_{1-6}$alkyl;

n is an integer ranging from 1 to 4;

p is an integer ranging from 0 to 1;

or a pharmaceutically acceptable salt thereof.

In a preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxycarbonyl, aryloxycarbonyl, aralkoxycarbonyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy, nitro or cyano; or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl.

In another preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino or aralkoxycarbonylamino.

In another preferred embodiment, the present invention is concerned with compounds of formula I wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, $C_{1-7}$alkyl-amino, arylamino, aralkylamino, $C_{1-7}$alkoxy$C_{1-7}$alkyl, aryloxy$C_{1-7}$alkyl, aralkoxy$C_{1-7}$alky or $C_{1-7}$alkylthio.

In another preferred embodiment, the present invention is concerned with compounds of formula I wherein $R^1$, $R^2$, $R^3$, and $R^4$ independently of each other represent hydrogen, halogen, perhalomethyl, or $C_{1-7}$alkyl, $C_{4-7}$-alkenynyl, $C_{2-7}$-alkenyl, $C_{2-7}$-alkynyl, aryl, aralkyl, hydroxy$C_{1-7}$alkyl, $C_{1-7}$alkoxy$C_{1-7}$alkyl, aryloxy$C_{1-7}$alkyl or aralkoxy$C_{1-7}$alkyl.

In another preferred embodiment, the present invention is concerned with compounds of formula I wherein $R^1$, $R^2$, $R^3$, and $R^4$ independently of each other represent hydrogen, halogen or $C_{1-7}$alkyl.

In another preferred embodiment, the present invention is concerned with compounds of formula I wherein $R^1$, $R^2$, $R^3$, and $R^4$ represent hydrogen.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl or aryl; optionally substituted with one or more halogen, perhalomethyl, hydroxy or cyano.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, heterocyclyl, heteroaryl, heteroaralkyl, heteroaryloxy, heteroaralkoxy, acyl, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino or aralkoxycarbonylamino.

In another preferred embodiment, the present invention is concerned with compounds of formula I wherein ring A represents a 5–6 membered cyclic ring, optionally substituted with one or more halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, aryl, aryloxy, aralkyl, aralkoxy, acyl, hydroxy$C_{1-7}$alkyl, amino, $C_{1-7}$alkyl-amino, arylamino, aralkylamino, $C_{1-7}$alkoxy$C_{1-7}$alkyl, aryloxy$C_{1-7}$alkyl, aralkoxy$C_{1-7}$alkyl or $C_{1-7}$alkylthio.

In another preferred embodiment, the present invention is concerned with compounds of formula I wherein ring A represents a 5–6 membered cyclic ring, optionally substituted with one or more halogen, perhalomethyl or $C_{1-7}$alkyl, $C_{4-7}$-alkenynyl, $C_{2-7}$-alkenyl, $C_{2-7}$-alkynyl, $C_{1-7}$alkoxy, aryl, aralkyl, hydroxy$C_{1-7}$alkyl, $C_{1-7}$alkoxy$C_{1-7}$alkyl, aryloxy$C_{1-7}$alkyl or aralkoxy$C_{1-7}$alkyl.

In another preferred embodiment, the present invention is concerned with compounds of formula I wherein ring A represents a 6 membered cyclic ring, optionally substituted with one or more chlorine or methyl groups.

In another preferred embodiment, the present invention is concerned with compounds of formula I wherein ring A represent a phenyl ring.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(CHR$^9$)—CH=CH—, —(CHR$^9$)—CH$_2$—CH$_2$—, —(C=O)—, —O—CH$_2$—O—, —(NR$^9$)—S(O$_2$)—, —(NR$^9$)—, —CH=(CR$^9$)—, —(CO)—(CHR$^9$)—, —CH$_2$—(SO)—, —S—, —(SO)—, —(SO$_2$)—, —CH$_2$—(SO$_2$)— or —CH$_2$—O—CH$_2$—, wherein R$^9$ is hydrogen, halogen, hydroxy, C$_{1-7}$alkyl, C$_{1-7}$alkoxy, aryl, aryloxy, aralkyl, aralkoxy, heterocyclyl, heteroaryl, heteroaralkyl, heteroaryloxy, heteroaralkoxy, hydroxyalkyl, amino, acylamino, C$_{1-7}$alkyl-amino, arylamino, aralkylamino, aminoC$_{1-7}$alkyl, C$_{1-7}$alkoxyC$_{1-12}$alkyl, aryloxyC$_{1-7}$alkyl, aralkoxyC$_{1-7}$alkyl, C$_{1-12}$alkylthio, thioC$_{1-7}$alkyl, C$_{1-7}$alkoxycarbonylamino, aryloxycarbonylamino or aralkoxycarbonylamino.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(CHR$^9$)—CH=CH—, —(CHR$^9$)—CH$_2$—CH$_2$—, —(C=O)—, —O—CH$_2$—O—, —(NR$^9$)—S(O$_2$)—, —(NR$^9$)—, —CH=(CR$^9$)—, —(CO)—(CHR$^9$)—, —CH$_2$—(SO)—, —S—, —(SO)—, —(SO$_2$)—, —CH$_2$—(SO$_2$)— or —CH$_2$—O—CH$_2$—, wherein R$^9$ is hydrogen, halogen, hydroxy, C$_{1-7}$alkyl, aryl, aralkyl, C$_{1-7}$alkoxyC$_{1-12}$alkyl, aryloxyC$_{1-7}$alkyl or aralkoxyC$_{1-7}$alkyl.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —(CHR$^9$)—CH=CH—, —(CHR$^9$)—CH$_2$—CH$_2$—, —(C=O)—, —O—CH$_2$—O—, —(NR$^9$)—S(O$_2$)—, —(NR$^9$)—, —CH=(CR$^9$)—, —(CO)—(CHR$^9$)—, —CH$_2$—(SO)—, —S—, —(SO)—, —(SO$_2$)—, —CH$_2$—(SO$_2$)— or —CH$_2$—O—CH$_2$—, wherein R$^9$ is hydrogen.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —O—CH$_2$—O—, —(NR$^9$)—, —S—, —(SO)—or —CH$_2$—O—CH$_2$—, wherein R$^9$ is hydrogen.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —(NR$^9$)—CH$_2$—, —O—CH$_2$—O—, —(NR$^9$)—, —S— or —CH$_2$—O—CH$_2$—, wherein R$^9$ is hydrogen.

In another preferred embodiment, the present invention is concerned with compounds of formula I wherein X is a valence bond, —(CHR$^9$)—, —(CHR$^9$)—CH$_2$—, —CH=CH—, —O—, —O—(CHR$^9$)—, —S—(CHR$^9$)—, —O—CH$_2$—O— or —S—, wherein R$^9$ is hydrogen.

In another preferred embodiment, the present invention is concerned with compounds of formula I wherein X is —S—.

In another preferred embodiment, the present invention is concerned with compounds of formula I wherein T is >C<.

In another preferred embodiment, the present invention is concerned with compounds of formula I wherein Z is —CH$_2$—, =CH—, >N—, —O—, —S—, >CO, >SO, >SO$_2$.

In another preferred embodiment, the present invention is concerned with compounds of formula I wherein Z is >N—.

In another preferred embodiment, the present invention is concerned with compounds of formula I wherein Q is —O—, —S—, >NR$^{18}$, wherein R$^{18}$ is hydrogen or C$_{1-7}$alkyl.

In another preferred embodiment, the present invention is concerned with compounds of formula I wherein Q is >NR$^{18}$, wherein R$^{18}$ is hydrogen.

In another preferred embodiment, the present invention is concerned with compounds of formula I wherein U is —O—.

In another preferred embodiment, the present invention is concerned with compounds of formula I wherein T==(Z)$_p$ represents a double bond.

In another preferred embodiment, the present invention is concerned with compounds of formula I wherein Ar represents arylene optionally substituted with one or more C$_{1-6}$alkyl or aryl.

In another preferred embodiment, the present invention is concerned with compounds of formula I wherein Ar represents phenyl.

In another preferred embodiment, the present invention is concerned with compounds of formula I wherein R$^5$ represents hydrogen, hydroxy, halogen, C$_{1-7}$alkoxy, C$_{1-7}$alkyl, C$_{4-7}$-alkenynyl, C$_{2-7}$-alkenyl, C$_{2-7}$-alkynyl or aralkyl, or R$^5$ forms a bond together with R$^6$.

In another preferred embodiment, the present invention is concerned with compounds of formula I wherein R$^5$ represents hydrogen or R$^5$ forms a bond together with R$^6$.

In another preferred embodiment, the present invention is concerned with compounds of formula I wherein R$^5$ represents hydrogen, hydroxy, halogen, C$_{1-7}$alkoxy, C$_{1-7}$alkyl, C$_{4-7}$-alkenynyl, C$_{2-7}$-alkenyl, C$_{2-7}$-alkynyl or aralkyl, or R$^5$ forms a bond together with R$^6$.

In another preferred embodiment, the present invention is concerned with compounds of formula I wherein R$^5$ represents hydrogen or R$^5$ forms a bond together with R$^6$.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl, C$_{2-7}$-alkynyl, aryl, aralkyl, C$_{1-7}$alkoxyC$_{1-7}$alkyl, C$_{1-7}$alkoxycarbonyl, aryloxycarbonyl, C$_{1-7}$alkylaminocarbonyl, arylaminocarbonyl, acyl, heterocyclyl, heteroaryl or heteroaralkyl groups.

In another preferred embodiment, the present invention is concerned with compounds of formula I wherein R$^7$ represents hydrogen, C$_{1-7}$alkyl, C$_{4-7}$-alkenynyl, C$_{2-7}$-alkenyl or C$_{2-7}$-alkynyl.

In another preferred embodiment, the present invention is concerned with compounds of formula I wherein R$^7$ represents C$_{1-2}$alkyl.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl, aralkyl, heterocyclyl, heteroaryl or heteroaralkyl groups; optionally substituted with one or more halogen, perhalomethyl, hydroxy, nitro or cyano.

In another preferred embodiment, the present invention is concerned with compounds of formula I wherein R$^8$ represents hydrogen, C$_{1-7}$alkyl, C$_{4-7}$-alkenynyl, C$_{2-7}$-alkenyl, C$_{2-7}$-alkynyl, aryl or aralkyl.

In another preferred embodiment, the present invention is concerned with compounds of formula I wherein R$^8$ represents hydrogen or C$_{1-2}$alkyl.

In another preferred embodiment, the present invention is concerned with compounds of formula I wherein Y represents oxygen, sulphur or $NR^{10}$, where $R^{10}$ represents hydrogen, $C_{1-7}$alkyl, aryl, hydroxy$C_{1-7}$alkyl or aralkyl groups.

In another preferred embodiment, the present invention is concerned with compounds of formula I wherein Y represents oxygen.

In another preferred embodiment, the present invention is concerned with compounds of formula I wherein n is an integer ranging from 2 to 3.

In another preferred embodiment, the present invention is concerned with compounds of formula I wherein p is 1.

In another preferred embodiment, the present invention is concerned with compounds of formula I wherein A is benzo.

In another preferred embodiment, the present invention is concerned with compounds of formula I wherein X is —O—.

In another preferred embodiment, the present invention is concerned with compounds of formula I wherein X is —S—.

In another preferred embodiment, the present invention is concerned with compounds of formula I wherein Z is —S— and p is 1.

In another preferred embodiment, the present invention is concerned with compounds of formula I wherein Z is —CH$_2$— and p is 1.

In another preferred embodiment, the present invention is concerned with compounds of formula I wherein X is =CH— and p is 1.

In another preferred embodiment, the present invention is concerned with compounds of formula I wherein T==(Z)$_p$ represents a single bond or a double bond.

In another preferred embodiment, the present invention is concerned with compounds of formula I wherein T is >CH—.

In another preferred embodiment, the present invention is concerned with compounds of formula I wherein T is >C<.

In another preferred embodiment, the present invention is concerned with compounds of formula I wherein Q is —O—.

In another preferred embodiment, the present invention is concerned with compounds of formula I wherein Q is —S—.

In another preferred embodiment, the present invention is concerned with compounds of formula I wherein Q is >NR$^{18}$, wherein R$^{18}$ is H.

In another preferred embodiment, the present invention is concerned with compounds of formula I wherein n is 2.

In another preferred embodiment, the present invention is concerned with compounds of formula I wherein U is —O—.

In another preferred embodiment, the present invention is concerned with compounds of formula I wherein Ar is phenylene.

In another preferred embodiment, the present invention is concerned with compounds of formula I wherein R$^5$ is H.

In another preferred embodiment, the present invention is concerned with compounds of formula I wherein R$^6$ is H.

In another preferred embodiment, the present invention is concerned with compounds of formula I wherein R$^7$ is ethyl.

In another preferred embodiment, the present invention is concerned with compounds of formula I wherein R$^8$ is H.

In another preferred embodiment, the present invention is concerned with compounds of formula I wherein p is 0.

In another preferred embodiment, the present invention is concerned with compounds of formula I wherein A is a five membered ring containing S.

In another preferred embodiment, the present invention is concerned with compounds of formula I wherein X is —(CHR$^9$)—CH$_2$—, wherein R$^9$ is H.

In another preferred embodiment, the present invention is concerned with compounds of formula I wherein X is —O—(CHR$^9$)—, wherein R$^9$ is H.

In another preferred embodiment, the present invention is concerned with compounds of formula I wherein X is —S—(CHR$^9$)—, wherein R$^9$ is H.

In another preferred embodiment, the present invention is concerned with compounds of formula I wherein X is —O—CH$_2$—O—.

Preferred compounds of the invention are:

2-Ethoxy-3-{4-[2-(11H-5-oxa-10-thia-dibenzo[a,d]cyclohepten-11-yloxy)-ethoxy]-phenyl}-propionic acid, 3-(4-[2-(Dibenzo[b,f]-1,4-thiazepin-11-ylamino)-ethoxy]-phenyl)-2-ethoxy-propinoic acid ethyl ester, 3-{4-[2-(Dibenzo[b,f][1,4]thiazepin-11-ylamino)-ethoxy]-phenyl}-2-ethoxy-propionic acid, 3-{4-[2-(10,11-Dihydro-dibenzo[b,f]thiepin-10-ylsulfanyl)-ethoxy]-phenyl}-2-ethoxy-propionic acid, 3-(4-[2-[5H-Dibenzo[a,d]cyclohepten-5-yloxy)-ethoxy]-phenyl)-2-ethoxy-propionic acid ethyl ester, 3-(4-[2-(6,11-Dihydrodibenzo[b,e]thiepin-11-yloxy)-ethoxy]-phenyl)-2-ethoxy-propionic acid ethyl ester, 3-(4-[2-(6,11-Dihydrodibenzo[b,e]thiepin-11-yloxy)-ethoxy]-phenyl)-2-ethoxy-propionic acid, 3-(4-[2-(6,11-Dihydrodibenzo[b,e]oxepin-11-yloxy)-ethoxy]-phenyl)-2-ethoxy-propionic acid ethyl ester, 3-(4-[2-(2,10-Dichloro-12H-5,7-dioxa-dibenzo[a,d]cycloocten-12-yloxy)-ethoxy]-phenyl)-2-ethoxy-propionic acid ethyl ester, 3-(4-[2-(2,10-Dichloro-12H-5,7-dioxa-dibenzo[a,d]cycloocten-12-yloxy)-ethoxy]-phenyl)-2-ethoxy-propionic acid, 2-Ethoxy-3-(4-[2-(2-methyl-9,10-dihydro-4H-1-oxa-3-aza-benzo[f]azulen-4-yloxy)-ethoxy]-phenyl)-propionic acid ethyl ester, 3-(4-[2-(10,11-Dihydro-5H-dibenzo[a,d]cyclohepten-5-yloxy)-ethoxy]-phenyl)-2-ethoxy-propanoic acid ethyl ester, 3-(4-[2-(10,11-Dihydro-5H-dibenzo[a,d]cyclohepten-5-yloxy)-ethoxy]-phenyl)-2-ethoxy-propanoic acid, 3-(4-[2-([10,11-dihydro-5H-dibenzo[a,d]cyclohepten-5-yl]-methyl-amino)-ethoxy]-phenyl)-2-ethoxypropanoic acid ethyl ester, and 3-(4-[2-([10,11-dihydro-5H-dibenzo[a,d]cyclohepten-5-yl]-methyl-amino)-ethoxy]-phenyl)-2-ethoxypropanoic acid;

or a pharmaceutically acceptable salt thereof.

Further, preferred compounds of the invention are:

2-Ethoxy-3-{4-[2-(11H-5-oxa-10-thia-dibenzo[a,d]cyclohepten-11-yloxy)-ethoxy]-phenyl}-propionic acid, 3-{4-[2-(Dibenzo[b,f][1,4]thiazepin-11-ylamino)-ethoxy]-phenyl)-2-ethoxy-propionic acid, and 3-{4-[2-(10,11-Dihydro-dibenzo[b,f]thiepin-10-ylsulfanyl)-ethoxy]-phenyl}-2-ethoxy-propionic acid;

or a pharmaceutically acceptable salt thereof.

In the above structural formulas and throughout the present specification, the following terms have the indicated meaning:

The terms "$C_{1-12}$-alkyl" as used herein, alone or in combination is intended to include those alkyl groups of the designated length in either a linear or branched or cyclic configuration. represents e.g. cyclopropyl, cyclobutyl, cyclopentyl, cyclohexyl, cycloheptyl and cyclooctyl and the like. Typical $C_{1-6}$-alkyl groups include, but are not limited to, methyl, ethyl, n-propyl, iso-propyl, butyl, iso-butyl, sec-butyl, tert-butyl, pentyl, iso-pentyl, hexyl, iso-hexyl, cyclopropyl, cyclobutyl, cyclopentyl, cyclohexyl, cycloheptyl and cyclooctyl-and the like.

The terms "$C_{2-n'}$-alkenyl" wherein n' can be from 3 through 15, as used herein, represents an olefinically unsaturated branched or straight group having from 2 to the specified number of carbon atoms and at least one double bond. Examples of such groups include, but are not limited to, vinyl, 1-propenyl, 2-propenyl, allyl, iso-proppenyl, 1,3-butadienyl, 1-butenyl, hexenyl, pentenyl, and the like.

The terms "$C_{2-n'}$-alkynyl" wherein n' can be from 3 through 15, as used herein, represent an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentynyl, 2-pentynyl and the like.

The terms "$C_{4-n'}$-alkenynyl" wherein n' can be from 5 through 15, as used herein, represent an unsaturated branched or straight hydrocarbon group having from 4 to the specified number of carbon atoms and both at least one double bond and at least one triple bond. Examples of such groups include, but are not limited to, 1-penten-4-yne, 3-penten-1-yne, 1,3-hexadiene-5-yne and the like.

The term "$C_{1-12}$-alkoxy" as used herein, alone or in combination is intended to include those $C_{1-12}$-alkyl groups of the designated length in either a linear or branched or cyclic configuration linked thorugh an ether oxygen having its free valence bond from the ether oxygen. Examples of linear alkoxy groups are methoxy, ethoxy, propoxy, butoxy, pentoxy and hexoxy. Examples of branched alkoxy are isoprpoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "$C_{1-6}$-alkoxycarbonyloxy" is intended to include the above defined $C_{1-6}$-alkoxy groups attached to a carbonyloxy moiety, eg. methoxycarbonyloxy, ethoxycarbonyloxy, etc..

As used herein the term "$C_{4-12}$-(cycloalkylalkyl)" represents a branched or straight alkyl group substituted at a carbon with a cycloalkyl group. Examples of such groups include, but are not limited to, cyclopropylethyl, cyclobutylmethyl, 2-(cyclohexyl)ethyl, cyclohexylmethyl, 3-(cyclopentyl)-1-propyl, and the like.

The term "$C_{1-12}$-alkylthio" as used herein, alone or in combination, refers to a straight or branched or cyclic monovalent substituent comprising a $C_{1-12}$-alkyl group linked through a divalent sulfur atom having its free valence bond from the sulfur atom and having 1 to 12 carbon atoms e.g. methylthio, ethylthio, propylthio, butylthio, pentylthio. Example of cyclic alkylthio are cyclopropylthio, cyclobutylthio, cyclopentylthio and cyclohexylthio.

The term "$C_{1-12}$alkylamino" as used herein, alone or in combination, refers to a straight or branched or cyclic monovalent substituent comprising a $C_{1-12}$-alkyl group linked through amino having a free valence bond from the nitrogen atom e.g. methylamino, ethylamino, propylamino, butylamino, pentylamino. Example of cyclic alkylamino are cyclopropylamino, cyclobutylamino, cyclopentylamino and cyclohexylamino.

The term "hydroxy$C_{1-12}$alkyl" as used herein, alone or in combination, refers to a $C_{1-12}$alkyl as defined herein whereto is attached a hydroxy group, e.g. hydroxyethyl, 1-hydroxypropyl, 2-hydroxypropyl etc.

The term "arylamino" as used herein, alone or in combination, refers to an aryl as defined herein linked through amino having a free valence bond from the nitrogen atom e.g. phenylamino, naphthylamino, etc.

The term "aralkylamino" as used herein, alone or in combination, refers to an aralkyl as defined herein linked through amino having a free valence bond from the nitrogen atom e.g. benzylamino, phenethylamino, 3-phenylpropylamino, 1-naphtylmethylamino, 2-(1-naphtyl) ethylamino and the like.

The term "amino$C_{1-12}$alkyl" as used herein, alone or in combination, refers to a $C_{1-12}$alkyl as defined herein whereto is attached an amino group, e.g. aminoethyl, 1-aminopropyl, 2-aminopropyl etc.

The term "aryloxycarbonyl" as used herein, alone or in combination, refers to an aryloxy as defined herein linked through a carbonyl having a free valence bond from the carbon atom, e.g. phenoxycarbonyl, 1-naphthyloxycarbonyl or 2-naphthyloxycarbonyl, etc.

The term "aralkoxycarbonyl" as used herein, alone or in combination, refers to an aralkoxy as defined herein linked through a carbonyl having a free valence bond from the carbon atom, e.g. benzyloxycarbonyl, phenethoxycarbonyl, 3-phenylpropoxycarbonyl, 1-naphthylmethoxycarbonyl, 2-(1-naphtyl)ethoxycarbonyl, etc.

The term "$C_{1-12}$alkoxy$C_{1-12}$alkyl" as used herein, alone or in combination, refers to a $C_{1-12}$alkyl as defined herein whereto is attached a $C_{1-12}$alkoxy as defined herein, e.g. methoxymethyl, ethoxymethyl, methoxyethyl, ethoxyethyl, etc.

The term "aryloxy$C_{1-12}$alkyl" as used herein, alone or in combination, refers to a $C_{1-12}$alkyl as defined herein whereto is attached an aryloxy as defined herein, e.g. phenoxymethyl, phenoxydodecyl, 1-naphthyloxyethyl, 2-naphthyloxypropyl, etc.

The term "aralkoxy$C_{1-12}$alkyl" as used herein, alone or in combination, refers to a $C_{1-12}$alkyl as defined herein whereto is attached an aralkoxy as defined herein, e.g. benzyloxymethyl, phenethoxydodecyl, 3-phenylpropoxyethyl, 1-naphthylmethoxypropyl, 2-(1-naphtyl) ethoxymethyl, etc.

The term "thio$C_{1-12}$alkyl" as used herein, alone or in combination, refers to a $C_{1-12}$alkyl as defined herein whereto is attached a group of formula —SR'" wherein R'" is hydrogen, $C_{1-6}$alkyl or aryl, e.g. thiomethyl, methylthiomethyl, phenylthioethyl, etc.

The term "$C_{1-12}$alkoxycarbonylamino" as used herein, alone or in combination, refers to a $C_{1-12}$alkoxycarbonyl as defined herein linked through amino having a free valence bond from the nitrogen atom e.g. methoxycarbonylamino, carbethoxyamino, propoxycarbonylamino, isopropoxycarbonylamino, n-butoxycarbonylamino, tert-butoxycarbonylamino, etc.

The term "aryloxycarbonylamino" as used herein, alone or in combination, refers to an aryloxycarbonyl as defined herein linked through amino having a free valence bond from the nitrogen atom e.g. phenoxycarbonylamino, 1-naphthyloxycarbonylamino or 2-naphthyloxycarbonylamino, etc.

The term "aralkoxycarbonylamino" as used herein, alone or in combination, refers to an aralkoxycarbonyl as defined herein linked through amino having a free valence bond from the nitrogen atom e.g. benzyloxycarbonylamino, phenethoxycarbonylamino, 3-phenylpropoxycarbonylamino, 1-naphthylmethoxycarbonylamino, 2-(1-naphtyl) ethoxycarbonylamino, etc.

The term "aryl" is intended to include aromatic rings, such as carboxylic aromatic rings selected from the group consisting of phenyl, naphtyl, (1-naphtyl or 2-naphtyl) optionally substituted with halogen, amino, hydroxy, $C_{1-6}$-alkyl or $C_{1-6}$-alkoxy.

The term "arylene" is intended to include divalent aromatic rings, such as carboxylic aromatic rings selected from the group consisting of phenylene, naphthylene, optionally substituted with halogen, amino, hydroxy, $C_{1-6}$-alkyl or $C_{1-6}$-alkoxy.

The term "halogen" means fluorine, chlorine, bromine or iodine.

The term "perhalomethyl" means trifluoromethyl, trichloromethyl, tribromomethyl or triiodomethyl.

The term "$C_{1-6}$-dialkylamino" as used herein refers to an amino group wherein the two hydrogen atoms independently are substituted with a straight or branched, saturated hydrocarbon chain having the indicated number of carbon atoms; such as dimethylamino, N-ethyl-N-methylamino, diethylamino, dipropylamino, N-(n-butyl)-N-methylamino, di(n-pentyl) amino, and the like.

The term "acyl" as used herein refers to a monovalent substituent comprising a $C_{1-6}$-alkyl group linked through a carbonyl group; such as e.g. acetyl, propionyl, butyryl, isobutyryl, pivaloyl, valeryl, and the like.

The term "acyloxy" as used herein refers to acyl as defined herein linked to an oxygen atom having its free valence bond from the oxygen atom e.g. acetyloxy, propionyloxy, butyryloxy, isobutyryloxy, pivaloyloxy, valeryloxy, and the like.

The term "$C_{1-12}$-alkoxycarbonyl" as used herein refers to a monovalent substituent comprising a $C_{1-12}$-alkoxy group linked through a carbonyl group; such as e.g. methoxycarbonyl, carbethoxy, propoxycarbonyl, isopropoxycarbonyl, n-butoxycarbonyl, sec-butoxycarbonyl, tert-butoxycarbonyl, 3-methylbutoxycarbonyl, n-hexoxycarbonyl and the like.

The term "a cyclic ring containing from 5 to 7 carbon atoms" as used herein refers to a monocyclic saturated or unsaturated or aromatic system, wherein the ring may be cyclopentyl, cyclopentenyl, cyclohexyl, phenyl or cycloheptyl.

The term "bicycloalkyl" as used herein refers to a monovalent substituent comprising a bicyclic structure made of 6–12 carbon atoms such as e.g. 2-norbornyl, 7-norbornyl, 2-bicyclo[2.2.2]octyl and 9-bicyclo[3.3.1]nonanyl.

The term "heteroaryl" as used herein, alone or in combination, refers to a monovalent substituent comprising a 5–6 membered monocyclic aromatic system or a 9–10, membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroarylene" as used herein, alone or in combination, refers to a divalent group comprising a 5–6 membered monocyclic aromatic system or a 9–10 membered bicyclic aromatic system containing one or more heteroatoms selected from nitrogen, oxygen and sulfur, e.g. furan, thiophene, pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine.

The term "heteroaryloxy" as used herein, alone or in combination, refers to a heteroaryl as defined herein linked to an oxygen atom having its free valence bond from the oxygen atom e.g. pyrrole, imidazole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indole, benzimidazole, benzofuran, pteridine and purine linked to oxygen.

The term "aralkyl" as used herein refers to a straight or branched saturated carbon chain containing from 1 to 6 carbons substituted with an aromatic carbohydride; such as benzyl, phenethyl, 3-phenylpropyl, 1-naphtylmethyl, 2-(1-naphtyl)ethyl and the like.

The term "aryloxy" as used herein refers to phenoxy, 1-naphthyloxy or 2-naphthyloxy.

The term "aralkoxy" as used herein refers to a $C_{1-6}$-alkoxy group substituted with an aromatic carbohydride, such as benzyloxy, phenethoxy, 3-phenylpropoxy, 1-naphthylmethoxy, 2-(1-naphtyl) ethoxy and the like.

The term "heteroaralkyl" as used herein refers to a straight or branched saturated carbon chain containing from 1 to 6 carbons substituted with a heteroaryl group; such as (2-furyl) methyl, (3-furyl)methyl, (2-thienyl)methyl, (3-thienyl)methyl, (2-pyridyl)methyl, 1-methyl-1-(2-pyrimidyl) ethyl and the like.

The term "heteroaralkoxy" as used herein refers to a heteroaralkyl as defined herein linked to an oxygen atom having its free valence bond from the oxygen atom, e.g. (2-furyl)methyl, (3-furyl)methyl, (2-thienyl)methyl, (3-thienyl)methyl, (2-pyridyl)methyl, 1-methyl-1-(2-pyrimidyl) ethyl linked to oxygen.

The term "$C_{1-6}$-alkylsulfonyl" as used herein refers to a monovalent substituent comprising a $C_{1-6}$-alkyl group linked through a sulfonyl group such as e.g. methylsulfonyl, ethylsulfonyl, n-propylsulfonyl, isopropyisulfonyl, n-butylsulfonyl, sec-butylsulfonyl, isobutylsulfonyl, tert-butylsulfonyl, n-pentylsulfonyl, 2-methylbutylsulfonyl, 3-methylbutylsulfonyl, n-hexylsulfonyl, 4-methylpentylsulfonyl, neopentylsulfonyl, n-hexylsulfonyl and 2,2-dimethylpropylsulfonyl.

The term "$C_{1-6}$-monoalkylaminosulfonyl" as used herein refers to a monovalent substituent comprising a $C_{1-6}$-monoalkylamino group linked through a sulfonyl group such as e.g. methylaminosulfonyl, ethylaminosulfonyl, n-propylaminosulfonyl, isopropylaminosulfonyl, n-butylaminosulfonyl, sec-butylaminosulfonyl, isobutylaminosulfonyl, tert-butylaminosulfonyl, n-pentylaminosulfonyl, 2-methylbutylaminosulfonyl, 3-methylbutylaminosulfonyl, n-hexylaminosulfonyl, 4-methylpentylaminosulfonyl, neopentylaminosulfonyl, n-hexylaminosulfonyl and 2,2-dimethylpropylaminosulfonyl.

The term "$C_{1-6}$-dialkylaminosulfonyl" as used herein refers to a monovalent substituent comprising a $C_{1-6}$-dialkylamino group linked through a sulfonyl group such as dimethylaminosulfonyl, N-ethyl-N-methylaminosulfonyl, diethylaminosulfonyl, dipropylaminosulfonyl, N-(n-butyl)-N-methylaminosulfonyl, di(n-pentyl)aminosulfonyl, and the like.

The term "$C_{1-6}$-alkylsulfinyl" as used herein refers to a monovalent substituent comprising a straight or branched $C_{1-6}$-alkyl group linked through a sulfinyl group (—S(=O)—); such as e.g. methylsulfinyl, ethylsulfinyl, isopropylsulfinyl, butylsulfinyl, pentylsulfinyl, and the like.

The term "acylamino" as used herein refers to an amino group wherein one of the hydrogen atoms is substituted with an acyl group, such as e.g. acetamido, propionamido, isopropylcarbonylamino, and the like.

The term "$(C_{3-6}$-cycloalkyl)$C_{1-6}$-alkyl" as used herein, alone or in combination, refers to a straight or branched, saturated hydrocarbon chain having 1 to 6 carbon atoms and being monosubstituted with a $C_{3-6}$-cycloalkyl group, the cycloalkyl group optionally being mono- or polysubstituted with $C_{1-6}$-alkyl, halogen, hydroxy or $C_{1-6}$-alkoxy; such as e.g. cyclopropylmethyl, (1-methylcyclopropyl) methyl, 1-(cyclopropyl)ethyl, cyclopentylmethyl, cyclohexylmethyl, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy; e.g. phenylthio, (4-methylphenyl)- thio, (2-chlorophenyl)thio, and the like.

The term "arylsulfinyl" as used herein refers to an aryl group linked through a sulfinyl group (—S(=O)—), the aryl group optionally being mono- or polysubstituted with $C_{1-6}$-alkyl, halogen, hydroxy or $C_{1-6}$-alkoxy; such as e.g. phenylsulfinyl, (4-chlorophenyl)sulfinyl, and the like.

The term "arylsulfonyl" as used herein refers to an aryl group linked through a sulfonyl group, the aryl group optionally being mono- or polysubstituted with $C_{1-6}$-alkyl, halogen, hydroxy or $C_{1-6}$-alkoxy; such as e.g. phenylsulfonyl, tosyl, and the like.

The term "$C_{1-6}$-monoalkylaminocarbonyl" as used herein refers to a monovalent substituent comprising a $C_{1-6}$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl.

The term "$C_{1-6}$-dialkylaminocarbonyl" as used herein refers to a monovalent substituent comprising a $C_{1-6}$-dialkylamino group linked through a carbonyl group such as dimethylaminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "$C_{1-6}$-monoalkylaminocarbonylamino" as used herein refers to an amino group wherein one of the hydrogen atoms is substituted with a $C_{1-6}$-monoalkylaminocarbonyl group, e.g. methylaminocarbonylamino, ethylaminocarbonylamino, n-propylaminocarbonylamino, isopropylaminocarbonylamino, n-butylaminocarbonylamino, sec-butylaminocarbonylamino, isobutylaminocarbonylamino, tert-butylaminocarbonylamino, and 2-methylbutylaminocarbonylamino.

The term "$C_{1-6}$-dialkylaminocarbonylamino" as used herein refers to an amino group wherein one of the hydrogen atoms is substituted with a $C_{1-6}$-dialkylaminocarbonyl group, such as dimethylaminocarbonylamino, N-ethyl-N-methylaminocarbonylamino, diethylaminocarbonylamino, dipropylaminocarbonylamino, N-(n-butyl)-N-methylaminocarbonylamino, di(n-pentyl)aminocarbonylamino, and the like.

As used herein, the phrase "heterocyclyl" means a monovalent saturated or unsaturated group being monocyclic and containing one or more, such as from one to four carbon atom(s), and from one to four N, O or S atom(s) or a combination thereof. The phrase "heterocyclyl" includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan); 5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a divalent heterocyclic group" means a divalent saturated or unsaturated system being monocyclic and containing one or more, such as from one to four carbon atom(s), and one to four N, O or S atom(s) or a combination thereof. The phrase a divalent heterocyclic group includes, but is not limited to, 5-membered heterocycles having one hetero atom (e.g. pyrrolidine, pyrroline); 5-membered heterocycles having two heteroatoms in 1,2 or 1,3 positions (e.g. pyrazoline, pyrazolidine, 1,2-oxathiolane, imidazolidine, imidazoline, 4-oxazolone); 5-membered heterocycles having three heteroatoms (e.g. tetrahydrofurazan); 5-membered heterocycles having four heteroatoms; 6-membered heterocycles with one heteroatom (e.g. piperidine); 6-membered heterocycles with two heteroatoms (e.g. piperazine, morpholine); 6-membered heterocycles with three heteroatoms; and 6-membered heterocycles with four heteroatoms.

As used herein, the phrase "a 5–6 membered cyclic ring" means an unsaturated or saturated or aromatic system containing one or more carbon atoms and optionally from one to four N, O or S atom(s) or a combination thereof. The phrase "a 5–6 membered cyclic ring" includes, but is not limited to, e.g. cyclopentyl, cyclohexyl, phenyl, cyclohexenyl, pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyi, pyrimidinyl, pyridazinyl, morpholinyl, thiomorpholinyl, isothiazolyl, isoxazolyl, oxazolyl, oxadiazolyl, thiadiazolyl, 1,3-dioxolanyl, 1,4-dioxolanyl, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having four heteroatoms; 6-membered heterocycles with one heteroatom (e.g. pyridine, quinoline, isoquinoline, phenanthridine, cyclohepta[b]pyridine); 6-membered heterocycles with two heteroatoms (e.g. pyridazines, cinnolines, phthalazines, pyrazines, pyrimidines, quinazolines, morpholines); 6-membered heterocycles with three heteroatoms (e.g. 1,3,5-triazine); and 6-membered heterocycles with four heteroatoms.

As used herein, the phrase,"5- or 6-membered nitrogen containing ring" refers to a monovalent substituent comprising a monocyclic unsaturated or saturated or aromatic system containing one or more carbon, nitrogen, oxygen or sulfur atoms or a combination thereof and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholinyl, thiomorpholinyl, isothiazolyl, isoxazolyl, oxazolyl, oxadiazolyl, thiadiazolyi, 1,3-dioxolanyl and 1,4-dioxolanyl.

Certain of the above defined terms may occur more than once in the above formula (Ia), and upon such occurence each term shall be defined independently of the other.

Pharmaceutically acceptable salts forming part of this invention include salts of the carboxylic acid moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, aluminum salts. Salts may include acid addition salts where appropriate which are, sulphates, nitrates, phosphates, perchlorates, borates, hydrohalides, acetates, tartrates, maleates, citrates, succinates, palmoates, methanesulplionates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The pharmaceutically acceptable salts are prepared by reacting the compound of formula (Ia) with 1 to 4 equivalents of a base such as sodium hydroxide, sodium methoxide, sodium hydride, potassium t-butoxide, calcium hydroxide, magnesium hydroxide and the like, in solvents lilke ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts whereever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or chiral bases such as brucine, cinchona alkaloids and their derivatives and the like. Commonly used methods are compiled by Jaques et al in "Enantiomers, Racemates and Resolution" (Wiley lnterscience, 1981). More specifically the compound of formula (Ia) may be converted to a 1:1 mixture of diastereomeric amides by treating with chiral amines, aminoacids, aminoalcohols derived from aminoacids; conventional reaction conditions may be employed to convert acid into an amide; the diastereomers may be separated either by fractional crystallization or chromatography and the stereoisomers of compound of formula (la) may be prepared by hydrolysing the pure diastereomeric amide.

Various polymorphs of compound of general formula (Ia) forming part of this invention may be prepared by crystallization of compound of formula (Ia) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The invention also relate to methods of preparing the above mentioned compounds, comprising:

a) reacting a compound of formula II

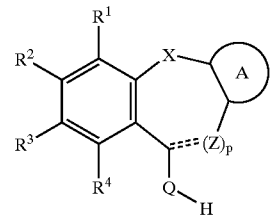

II wherein $R^1$–$R^4$, A, X, Z, p and Q are defined as above, with a compound of formula III

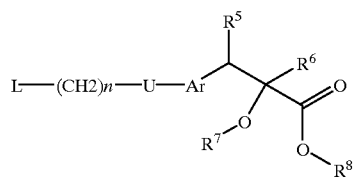

III wherein L is a leaving group such as halogen, p-toluenesulfonate, methanesulfonate and the like and wherein n, U, Ar, $R^5$–$R^8$ are defined as above except that $R^8$ is not H, to obtain a compound of formula (Ia) wherein n, p, Ar, $R^1$–$R^8$, A, X, Z, U and Q are defined as above except that $R^8$ is not H.

b) reacting a compound of formula IV

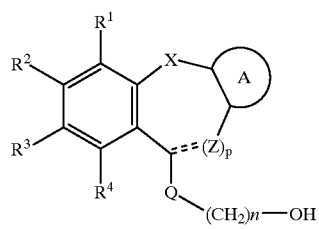

IV wherein $R^1$–$R^4$, A, X, Z, Q, p and n are defined as above, with a compound of formula V

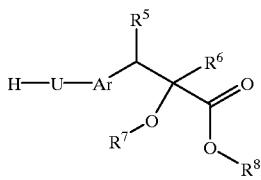

V wherein U, Ar and $R^5$–$R^8$ are defined as above except that $R^8$ is not H, by using suitable coupling agents such as dicyclohexyl urea, triaryiphosphinel dialkylazadicarboxylate such as $PPh_3$/ DEAD (Diethylazodicarboxylate) and the like, to obtain a compound of formula I, wherein n, p, Ar, $R^1$–$R^8$, A, X, Z, U and Q are defined as above except that $R^8$ is not H, and U is not C.

c) reacting a compound of formula VI

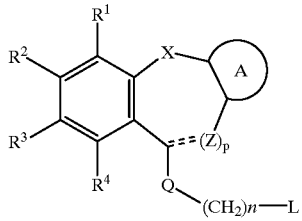

VI wherein L is a leaving group such as halogen, p-toluenesulfonate, methanesulfonate and the like and wherein $R^1$–$R^4$, A, X, Z, Q, p and n are defined as above, with an compound of formula V

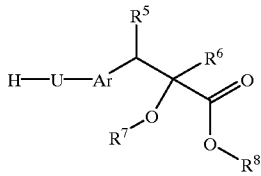

V wherein U, Ar and $R^5$–$R^8$ are defined as above except that $R^8$ is not H. to obtain a compound of formula (Ia) wherein n, p, Ar, $R^1$–$R^8$, A, X, Z, U and Q are defined as above except that $R^8$ is not H and U is not C.

d) reacting a compound of formula VII

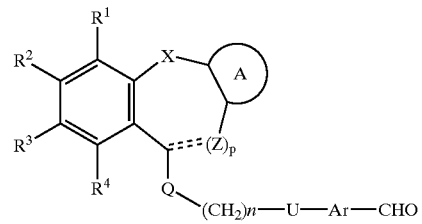

VII wherein $R^1$–$R^4$, A, X, Z, Q, U, Ar, p, and n are defined as above, with an compound of formula VIII

VIII wherein $R^6$–$R^8$ are defined as above except that $R^8$ is not H, to obtain the β-hydroxy aldol product, which may be dehydroxylated or dehydrated to obtain a compound of formula (Ia) wherein n, p, Ar, $R^1$–$R^8$, A, X, Z, U and Q are defined as above except that $R^8$ is not H.

e) reacting a compound of formula VII

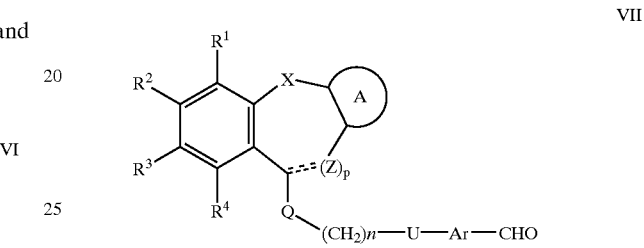

VII wherein $R^1$–$R^4$, A, X, Q, Z, U, Ar, p and n are defined as above, with an compound of formula IX

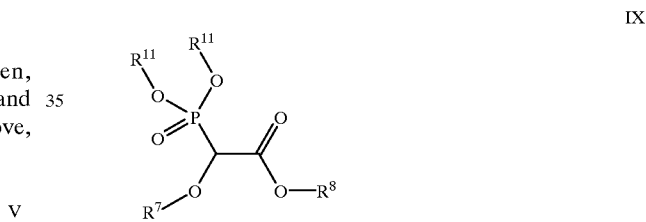

IX wherein $R^7$ and $R^8$ are defined as above except that $R^8$ is not H, and wherein $R^{11}$ is a lower alkyl group to obtain a compound of formula (Ia) wherein n, p, Ar, $R^1$–$R^4$, $R^7$–$R^8$, A, X, Z, U and Q are defined as above except that $R^8$ is not H and wherein $R^5$ forms a bond together with $R^6$.

f) hydrogenation of a compound of formula X

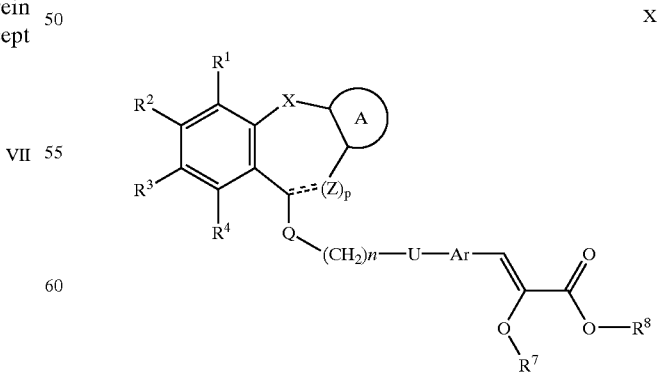

X wherein n, p, Ar, $R^1$–$R^4$, $R^7$–$R^8$, A, X, Z, U and Q are defined as above except that $R^8$ is not H, to obtain a compound of formula (Ia) wherein n, p, Ar, $R^1$–$R^4$, $R^7$–$R^8$, A, X, Z, U and Q are defined as above except that $R^8$ is not H and wherein $R^5$ and $R^6$ is hydrogen.

g) reacting a compound of formula XI

XI

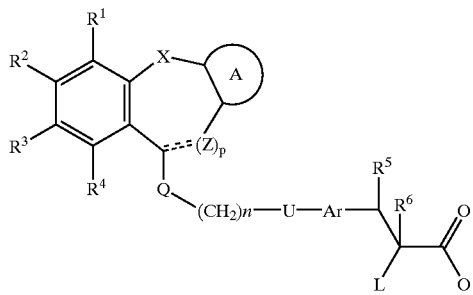

wherein L is a leaving group such as halogen and $R^1$–$R^8$, A, X, Q, Z, U, p and n are defined as above except that $R^8$ is not H, with an alcohol of formula XII

XII

HO—$R^7$ wherein $R^7$ is defined as above, to obtain a compound of formula (Ia) wherein n, p, Ar, $R^1$–$R^8$, A, X, Z, U and Q is defined as above except that $R^8$ is not H.

h) reacting a compound of formula XIII

XIII

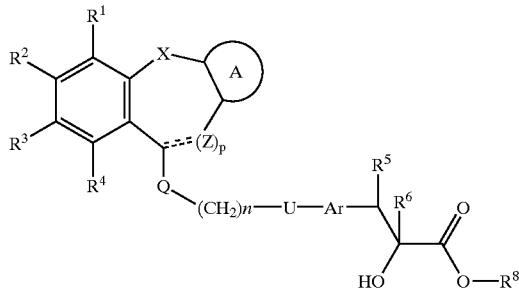

wherein n, p, Ar, $R^1$–$R^6$, A, X, Q, Z, U and Q is defined as above and wherein $R^8$ is defined as above except that $R^8$ is not H, with a compound of formula XIV

XIV

Hal—$R^7$ wherein $R^7$ is defined as above and wherein "Hal" represents Cl, Br, or I to obtain a compound of formula (Ia) wherein n, p, Ar, $R^1$–$R^8$, A, X, Z, U and Q is defined as above except that $R^8$ is not H.

i) reacting a compound of formula VI

VI

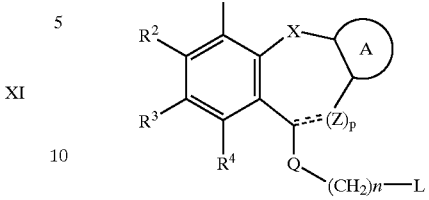

wherein L is a leaving group such as halogen, p-toluenesulfonate, methanesulfonate and the like and wherein $R^1$–$R^4$, A, X, Q, Z, p and n are defined as above, with a nucleophilic compound of formula XV

XV

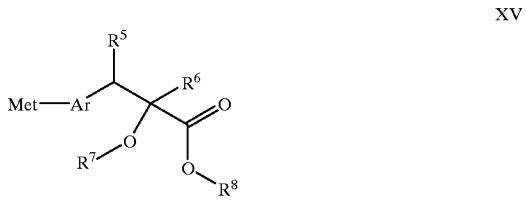

wherein "Met" is a metal such as zinc or copper, carrying suitable ligands chosen preferentially from trifluoromethanesulfonate, halide or $C_1$–$C_6$ alkyl, to obtain a compound of formula (Ia) wherein n, p, Ar, $R^1$–$R^8$, $R^7$, A, X and Q is defined as above except that $R^8$ is not H, and U is C.

j) saponification a compound of formula XVI

XVI

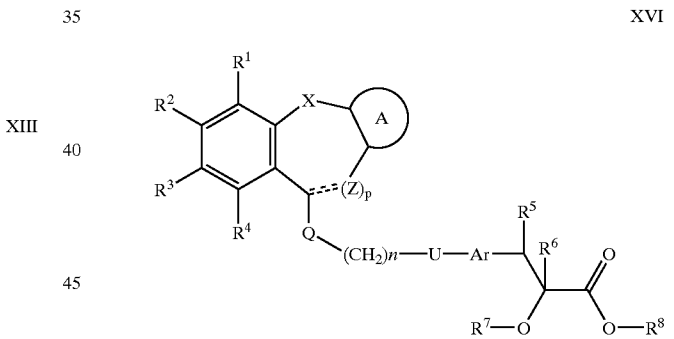

wherein n, p, Ar, $R^1$–$R^8$, A, X, Z, U and Q is defined as above except that $R^8$ is not H, to obtain a compound of formula (Ia) wherein n, Ar; $R^1$–$R^7$, A, X, Z and Q is defined as above and wherein $R^8$ is H.

The starting materials are commercially available or readily prepared by methods familiar to those skilled in the art.

Pharmacological Methods

In vitro PPAR alpha and PPAR gamma activation activity

Principle

The PPAR gene transcription activation assays were based on transient transfection into human HEK293 cells of two plasmids encoding a chimeric test protein and a reporter protein respectively. The chimeric test protein was a fusion of the DNA binding domain (DBD) from the yeast GAL4 transcription factor to the ligand binding domain (LBD) of the human PPAR proteins. The PPAR LBD harbored in addition to the ligand binding pocket also the native activation domain (activating function 2=AF2) allowing the fusion protein to function as a PPAR ligand dependent transcription factor. The GAL4 DBD will force the fusion protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand, luciferase protein will be produced in amounts corresponding to the activation of the PPAR protein. The amount of luciferase protein is measured by light emission after addition of the appropriate substrate.

Methods

Cell culture and transfection: HEK293 cells were grown in DMEM+10% FCS, 1% PS. Cells were seeded in 96-well plates the day before transfection to give a confluency of 80% at transfection. 0,8 µg DNA per well was transfected using FuGene transfection reagent according to the manufacturers instructions (Boehringer-Mannheim). Cells were allowed to express protein for 48 h followed by addition of compound.

Plasmids: Human PPAR α and γ was obtained by PCR amplification using cDNA templates from liver, intestine and adipose tissue respectively. Amplified cDNAs were cloned into pCR2.1 and sequenced. The LBD from each isoform PPAR was, generated by PCR (PPARα: aa 167 - C-term; PPARγ: aa 165 - C-term) and fused to GAL4-DBD by subcloning fragments in frame into the vector pM1 generating the plasmids pM1αLBD and pM1γLBD. Ensuing fusions were verified by sequencing. The reporter was constructed by inserting an oligonucleotide encoding five repeats of the Gal4 recognition sequence into the pGL2 vector (Promega).

Compounds: All compounds were dissolved in DMSO and diluted 1:1000 upon addition to the cells. Cells were treated with compound (1:1000 in 200 µl growth medium including delipidated serum) for 24 h followed by luciferase assay.

Luciferase assay: Medium including test compound was aspirated and 100 µl PBS incl. 1 mM Mg++ and Ca++ was added to each well. The luciferase assay was performed using the LucLite kit according to the manufacturers instructions (Packard Instruments). Light emission was quantified by counting SPC mode on a Packard Instruments top-counter.

Pharmaceutical Compositions

In another aspect, the present invention includes within its scope pharmaceutical compositions comprising, as an active ingredient, an effective amount of at least one of the compounds of formula (Ia) or a pharmaceutically acceptable salt thereof together with a pharmaceutically acceptable carrier or diluent.

Pharmaceutical compositions containing a compound of the present invention may be prepared by conventional techniques, e.g. as described in *Remington: The Science and Practise of Pharmacy,* 19$^{th}$ Ed., 1995. The compositions may appear in conventional forms, for example capsules, tablets, aerosols, solutions, suspensions or topical applications.

Typical compositions include a compound of formula (Ia) or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or nonaqueous liquid suspension or solution.

For nasal administration, the preparation may contain a compound of formula (Ia) dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 5 mg |
| Colloidal silicon dioxide (AEROSIL) | 1.5 mg |
| Cellulose, microcryst. (AVICEL) | 70 mg |
| Modified cellulose gum (AC-DI-DOL) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a mammal, especially a human in need of such treatment, prevention, elimination, alleviation or amelioration of diseases related to the regulation of blood sugar. Such mammals include also animals, both domestic animals, e.g. household pets, and non-domestic animals such as wildlife.

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients it may frequently be necessary to begin with a dosage of from about 2 to about 70 mg per day and when the condition is under control to reduce the dosage as low as from about 0.1 to about 10 mg per day. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.1 to about 100 mg of active ingredient together with a pharmaceutically acceptable carrier per unit dosage.

Usually, dosage forms suitable for oral, nasal, pulmonal or transdermal administration comprise from about 0.001 mg to about 100 mg, preferably from about 0.01 mg to about 50 mg of the compounds of formula (Ia) admixed with a pharmaceutically acceptable carrier or diluent.

In a further aspect, the present invention relates to a method of treating and/or preventing type I or type II diabetes.

In a still further aspect, the present invention relates to the use of one or more compounds of formula (Ia) or pharmaceutically acceptable salts thereof for the preparation of a medicament for the treatment and/or prevention of type I or type II diabetes.

Any novel feature or combination of features described herein is considered essential to this invention.

The invention will now be described in further detail with reference to the following examples. The examples are provided for illustrative purposes, and are not to be construed as limiting the scope of the invention in any way.

EXAMPLE 1

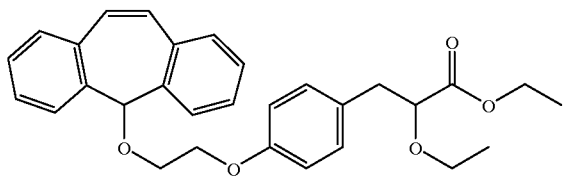

3-(4-[2-[5H-Dibenzo[a,d]cyclohepten-5-yloxy)-ethoxy]-phenyl)-2-ethoxy-propionic acid ethyl ester a)
Dibenzosuberenol (2.08 g, 10 mmol) was dissolved in dry THF (20 mL) at 0° C. Sodium hydride (1.0 g of 50% mineral oil dispersion, 20 mmol) was added. After 10 min. tert-butylbromoacetate (4.0 g, 20.0 mmol) was added over a period of 20 min and then stirred for 1 h. The reaction mixture was quenched with water at 0° C. and the product extracted with ethyl acetate. The combined extracts were dried (MgSO₄), and concentrated in vacuo. The product was-redissolved in ether (20 mL) and added dropwise to an ether (15 mL) suspension of lithium aluminium hydride (190 mg, 5.0 mmol). The reaction was stirred 16 h at room temperature, quenched with water. The ether solution was washed with water, dried, and concentrated in vacuo to give 1.3 g (50%) of 2-(5H-dibenzo[a,d]cyclohepten-5-yloxy)-ethanol.

b)
Under a nitrogen atmosphere, 2-(5H-dibenzo[a,d]cyclohepten-5-yloxy)-ethanol (400 mg, 1.6 mmol), tributylphosphine (480 mg, 2.4 mmol) and 2-ethoxy-3-(4-hydroxy-phenyl)-propionic acid ethyl ester (380 mg, 1.6 mmol) were successively dissolved in dry benzene (10 mL). Solid azodicarboxylic dipiperidine (ADDP) (480 mg, 2.4 mmol) was added under stirring at 0° C. to the solution. After 10 min, the reaction mixture was brought to room temperature and the stirring was continued for 2 h. The mixture was added water and the product extracted with ethyl acetate. The combined organic phases was dried (MgSO₄), and concentrated in vacuo. The residue was purified chromatography eluting with ethyl acetate/hexane (1:9) to give 350 mg (47%) of the title compound: MS 472 (M⁺).

EXAMPLE 2

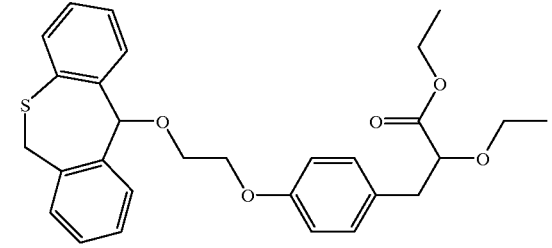

3-(4-[2-(6,11-Dihydrodibenzo[b,e]thiepin-11-yloxy)-ethoxy]-phenyl)-2-ethoxy-propionic acid ethyl ester a)
6,11-Dihydrodibenzo[b,e]thiepin-11-ol (1.14 g, 5 mmol) was dissolved in dry THF (25 mL) at 0° C. Sodium hydride (0.24 g of 50% mineral oil dispersion, 5 mmol) was added portionwise at 0° C. and then refluxed for 30 min. tert-Butylbromoacetate (980 mg, 5.0 mmol) in dry THF (10 mL) was added over a period of 20 min followed by a 30 min reflux. The reaction mixture was quenched with water at 0° C. and the product extracted with ether. The combined extracts were dried (MgSO$_4$), and concentrated in vacuo. The product was redissolved in ether and added dropwise to an ether (15 mL) suspension of lithium aluminium hydride (190 mg, 5.0 mmol). The reaction was stirred 16 h at room temperature, quenched with water, cooled, and filtered through Decalit. The ether solution was washed with saturated NaCl, dried, and purified by chromatography eluting with ethyl acetate/dichloromethan (1:10) to give 850 mg (63%) of 2-(6,11-dihydrodibenzo[b,e]thiepin-11-yloxy)-ethanol. $^1$H NMR (300 MHz, CDCl$_3$) δ3.55–3.70 (m, 2H), 3.75-3.85 (m, 2H), 4.00 (bs,1H), 4.85 (bs, 1H), 5.55 (bs, 1H), 7.03–7.13 (m, 3H), 7.13–7.48 (m, 5H).

b)

Under a nitrogen atmosphere, 2-(6,11-dihydrodibenzo[b,e]thiepin-11-yloxy)-ethanol (340 mg, 1.25 mmol), tributylphosphine (280 mg, 1.37 mmol) and 2-ethoxy-3-(4-hydroxy-phenyl)-propionic acid ethyl ester (330 mg, 1.37 mmol) were successively dissolved in dry benzene (10 mL). Solid azodicarboxylic dipiperidine (ADDP) (350 mg, 1.37 mmol) was added under stirring at 0° C. to the solution. After 10 min, the reaction mixture was brought to room temperature and the stirring was continued for 16 h. Heptane (10 mL) was added to the reaction mixture and dihydro-ADDP separated out was filtered off. After evaporation of the solvent the product was purified chromatography eluting with ethyl acetate/heptane (1:4) to give 460 mg (75%) of the title compound: $^1$H NMR (300 MHz, CDCl$_3$) δ1.15 (t, 3H), 1.25 (t, 3H), 2.95 (d, 2H), 3.30–3.40 (m, 1H), 3.55–3.65 (m, 1H), 2.85 (t, 2H), 3.95 (t, 1H), 4.10–4.22 (m, 4H), 4.5–5.1 (bs, 1H), 5.60–5.75 (bs, 1H), 6.82,(d, 2H), 7.05–7.50 (m, 10H).

EXAMPLE 3

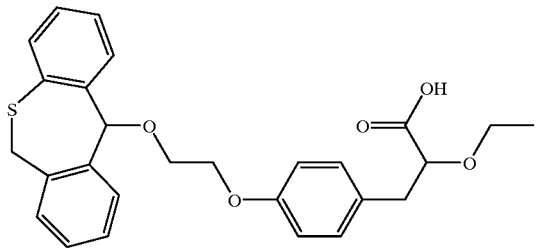

3-(4-[2-(6,11-Dihydrodibenzo[b,e]thiepin-11-yloxy)-ethoxy]-phenyl)-2-ethoxy-propionic acid 3-(4-[2-(6,11-Dihydrodibenzo[b,e]thiepin-11-yloxy)-ethoxy]-phenyl)-2-ethoxy-propionic acid ethyl ester (example 2) (220 mg, 0.44 mmol) in ethanol (5 mL) was added NaOH 1N (0.9 mL, 0.9 mmol). The mixture was stirred at room temperature for 16 h. The ethanol was evaporated of and pH adjusted with HCl 1N to pH 1. After extraction with dichloromethane the product was purified by chromatography, using dichloromethane/methanol (9:1) as eluent, to give 126 mg (62%) of the title compound: $^1$H NMR (300 MHz, CDCl$_3$) δ1.15 (t, 3H), 2.85–3.10 (m, 2H), 3.32–3.42 (m,$_1$ H), 3.52–3.65 (m,$_1$ H), 2.85 (t, 2H), 3.95–4.05 (m, 1H), 4.10–4.22 (m, 2H), 4.5–5.1 (bs, 1H), 5.60–5.75 (bs, 1H), 6.82 (d, 2H), 7.05–7.50 (m, 10H).

EXAMPLE 4

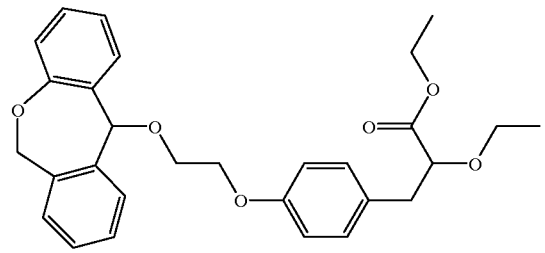

3-(4-[2-(6,11-Dihydrodibenzo[b,e]oxepin-11-yloxy)-ethoxy]-phenyl)-2-ethoxy-propionic acid ethyl ester a)

6,11-Dihydrodibenzo[b,e]oxepin-11-ol (1.06 g, 5 mmol) was dissolved in dry THF (25 mL) at 0° C. Sodium hydride (0.24 g of 50% mineral oil dispersion, 5 mmol) was added portionwise at 0° C. and then refluxed for 30 min. tert-Butylbromoacetate (980 mg, 5.0 mmol) in dry THF (10 mL) was added over a period of 20 and the mixture stirred at 35° C. for 16 h. The reaction mixture was quenched with water at 0° C. and the product extracted with ether. The combined extracts were dried (MgSO$_4$), and concentrated in vacuo. The product was redissolved in ether and added dropwise to an ether (15 mL) suspension of lithium aluminium hydride (190 mg, 5.0 mmol). The reaction was stirred 48 h at room temperature, quenched with water, cooled, and filtered through Decalit. The ether solution was washed with saturated NaCl, dried, and purified by chromatography eluting with ethyl acetate/dichloromethan (1:10) to give 267 mg (21%) of 2-(6,11-dihydrodibenzo[b,e]oxepin-11-yloxy)-ethanol.

b)

Under a nitrogen atmosphere, 2-(6,11-dihydrodibenzo[b,e]oxepin-11-yloxy)-ethanol (256 mg, 1.0 mmol), tributylphosphine (223 mg, 1.1 mmol) and 2-ethoxy-3-(4-hydroxy-phenyl)-propionic acid ethyl ester (262 mg, 1.1 mmol) were successively dissolved in dry benzene (10 mL). Solid azodicarboxylic dipiperidine (ADDP) (278 mg, 1.1 mmol) was added under stirring at 0° C. to the solution. After 10 min, the reaction mixture was brought to room temperature and the stirring was continued for 16 h. Heptane (10 mL) was added to the reaction mixture and dihydro-ADDP separated out was filtered off. After evaporation of the solvent the product was purified chromatography eluting with ethyl acetate/heptane (1:4) to give 175 mg (37%) of the title compound: $^1$H NMR (300 MHz, CDCl$_3$)δ1.15 (t, 3H), 1.25 (t, 3H), 2.93 (d, 2H), 3.30–3.40 (m, 1H), 3.55–3.65 (m, 1H), 3.65–3.75 (m, 1H),3.78–3.88 (m,1 H), 3.95 (t, 1H), 4.10 (t, 2H), 4.15 (q, 2H), 4.85 (d, 1H), 5.25 (s, 1H), 6.15 (d, 1H), 6.75 (d,2H), 6.85–6.95 (m, 2H), 7.10 (d, 2H), 7.15–7.40 (m, 6H).

EXAMPLE 5

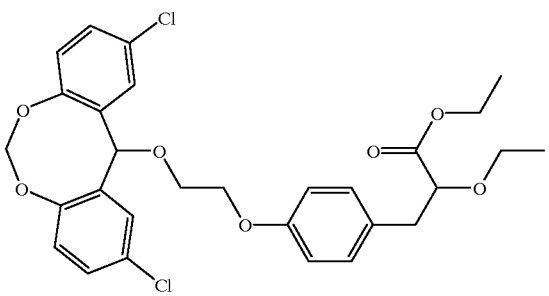

3-(4-[2-(2,10-Dichloro-12H-5,7-dioxa-dibenzo[a,d]cycloocten-1 2-yloxy)-ethoxy]-phenyl)-2-ethoxy-propionic acid ethyl ester a)
To a solution of bis-(5-chloro-2-hydroxyphenyl)-methane (24.4 g, 90.7 mmol) in dry DMF (340 mL) was added diiodomethane (25.5 g, 95.0 mmol) and potassium carbonate (18.2 g, 132 mmol). The mixture was stirred at 105° C. for 16 h. The mixture was added to ice water (1200 mL) and stirred for 30 min. The product was isolated by filtration, and washed with water and suspended in a mixture of ethanol (200 mL) and 4N NaOH (50 mL). The mixture was heated at 80° C. for 1 h. The mixture was added to water (600 mL) and 21.45 g (84%) 2,10-dichloro-12H-dibenzo[d,g][1,3]-dioxocin was isolated by filtration.

b)
To a solution of 2,10-dichloro-12H-dibenzo[d,g][1,3)-dioxocin (21.4 g, 76.1 mmol) and N-bromosuccinimide (13.5 g, 76.1 mmol) in tetrachloromethane (275 mL) was added azobisisobutyronitrile (200 mg, 1.2 mmol). The mixture was heated at 80° C. for 24 h. Another 3 x azobisisobutyronitrile (200 mg, 1.2 mmol) was added within the 24 h. The mixture was filtrated and the solution phase concentrated in vacuo. The residue was added dichloromethane (30 mL) and ether (100 mL). The mixture was filtered and the solution phase concentraded in vacuo. The residue was submitted to flash chromatography eluting with heptane/ethyl acetate (3:1) to give 7.4 g (27%) of 12-bromo-2,10-dichloro-12H-5,7-dioxa-dibenzo[a,d]cyclooctene.

c)
A mixture of 12-bromo-2,10-dichloro-12H-5,7-dioxa-dibenzo[a,d]cyclooctene (900 mg, 2.5 mmol), 2-bromoethanol (3.75 g, 30 mmol) and potassium carbonate (1.0 g, 7.2 mmol) in dichloromethane (10 mL) was heated at 120° C. for 4 h. The reaction mixture was concentrated in vacuo, added water (25 mL) and the product extracted with ethyl acetate (3×25 mL). The combined organic phases were dried (MgSO$_4$), filtered and evaporated to give 832 mg (82%) of 12-(2-bromo-ethoxy)-2,10-dichloro-12H-5,7-dioxa-dibenzo[a,d]cyclooctene.

d)
To a solution of 12-(2-bromo-ethoxy)-2,10-dichloro-12H-5,7-dioxa-dibenzo[a,d]cyclooctene (404 mg, 1.0 mmol) and 2-ethoxy-3-(4-hydroxy-phenyl)-propionic acid ethyl ester (238 mg, 1.0 mmol) in dry toluene (6 mL) was added potassium carbonate (276 mg, 2.0 mmol) and 18-crown-6 (528 mg, 2.0 mmol). The mixture was heated at 60° C. for 16 h. The mixture was filtered, and concentrated in vacuo. The residue was submitted to flash chromatography using toluene/ethyl acetate (19:1) as eluent to give 297 mg (53%) of the title compound; $^1$H NMR (300 MHz, CDCl$_3$) δ1.18 (t, 3H), 1.25 (t, 3H), 2.96 (d, 2H), 3.30–3.42 (m, 1H), 3.55–3.65 (m, 1H), 3.90–3.95 (m, 2H), 4.0 (t, 1H), 4.15–425 (m, 4H), 4.55 (d, 1H), 5.87 (d, 1H), 6.18 (s, 1H), 6.88–6.95 (m, 4H), 7.10–7.25 (m, 4H), 7.60 (d, 2H).

EXAMPLE 6

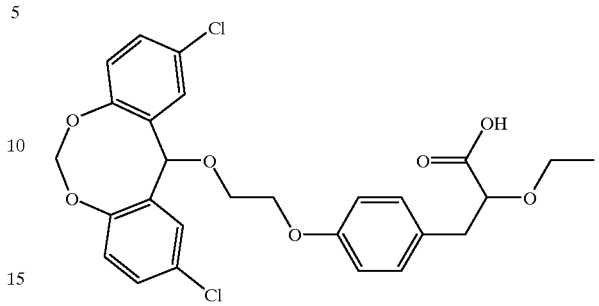

3-(4-[2-(2,10-Dichloro-12H-5,7-dioxa-dibenzo[a,d]cycloocten-12-yloxy)-ethoxy]-phenyl)-2-ethoxy-propionic acid 3-(4-[2-(2,10-Dichloro-12H-5,7-dioxa-dibenzo[a,d]cycloocten-12-yloxy)-ethoxy]-phenyl)-2-ethoxy-propionic acid ethyl ester (example 5) (450 mg, 0.8 mmol) in ethanol (8 mL) was added NaOH 1N (4.0 mL, 4.0 mmol). The mixture was stirred at room temperature for 16 h. The sodium salt of the title compound was isolated by filtration and washed with ethanol/water to give 272 mg (61%): m.p. 240–241° C. $^1$H NMR (300 MHz, DMSO-d$_6$) δ0.95 (t, 3H), 2.55–2.65 (m, 1H), 2.80–2.88 (m, 1H), 3.05–3.15 (m, 1H), 3.48–3.60 (m, 2H), 3.80–3.90 (m, 2H), 4.15–4.25 (m, 2H), 4.65 (d, 1H), 5.90 (d, 1H), 6.13 (s, 1H), 6.85 (d, 2H), 7.05 (d, 2H), 7.15 (d, 2H), 7.23–7.30 (m, 2H), 7.55–7.58 (m, 2H).

EXAMPLE 7

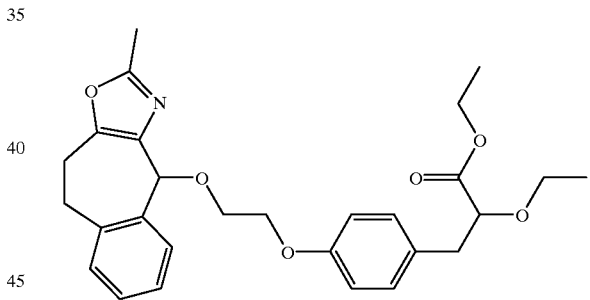

2-Ethoxy-3-(4-[2-(2-methyl-9,10-dihydro-4H-1-oxa-3-aza-benzo[f]azulen-4-yloxy)-ethoxy]-phenyl)-propionic acid ethyl ester a)
To an ice cooled solution of oxazol (1.08 g, 5.0 mmol) in dry THF (50 mL) was added sodium hydride (500 mg of 60% mineral oil dispersion, 10 mmol). After stirring for 20 min. tert-butyl bromoacetate (1.95 g, 10 mmol) was added. Stirring at room temperature for 1 h. The reaction mixture was quenched with water and the product extracted with ethyl acetate (2×50 mL). The combined organic phases were dried (MgSO$_4$), filtered and concentrated in vacuo to give 1.47 g (90%) of (2-methyl-9,10-dihydro-4H-1-oxa-3-aza-benzo[f]azulen-4-yloxy)-acetic acid tert-butyl ester.

b)
To a solution of (2-methyl-9,10-dihydro-4H-1-oxa-3-aza-benzo[f]azulen-4-yloxy)-acetic acid tert-butyl ester (1.4 g, 4.3 mmol) in dry ether (10 mL) was added a suspension of lithium aluminum hydride (245 mg, 6.5 mmol) in dry ether (40 mL). Stirring at room temperature for 1.5 h. The reaction was quenched with water an the product extracted with ether. The combined ether phases were dried MgSO₄, filtered and concentrated in vacuo to give 900 mg (91%) of 2-(2-methyl-9,10-dihydro-4H-1-oxa-3-aza-benzo[t]azulen-4-yloxy)-ethanol.

c)

Under a nitrogen atmosphere, 2-(2-methyl-9,10-dihydro-4H-1-oxa-3-aza-benzo[f]azulen-4-yloxy)-ethanol (400 mg, 1.6 mmol), tributylphosphine (480 mg, 2.4 mmol) and 2-ethoxy-3-(4-hydroxy-phenyl)-propionic acid ethyl ester (380 mg, 1.6 mmol) were successively dissolved in dry benzene (10 mL). Solid azodicarboxylic dipiperidine (ADDP) (480 mg, 2.4 mmol) was added under stirring at 0° C. to the solution. After 10 min, the reaction mixture was brought to room temperature and, the stirring was continued for 16 h. The mixture was added water and the product extracted with ethyl acetate. The combined organic phases was dried (MgSO₄), and concentrated in vacuo. The residue was purified chromatography eluting with petroleum ether/ethyl acetate (1:1) to give 300 mg (40%) of the title compound: ¹H NMR (300 MHz, CDCl₃) δ1.15 (t, 3H). 1.20 (t, 3H), 22.38 (s, 3H), 2.60–2.85 (m, 2H), 2.90–3.05 (m, 3H), 3.25–3.38 (m, 1H), 3.52–3.65 (m, 1H), 3.65–3.75 (m, 1H). 3.75–3.90 (m, 2H), 3.95 (t, 1H), 4.05 (t, 2H), 4.15 (q, 2H), 5.25 (s, 1H), 6.75 (d, 2H), 7.10 (d, 2H), 7.13–7.30 (m, 4H).

EXAMPLE 8

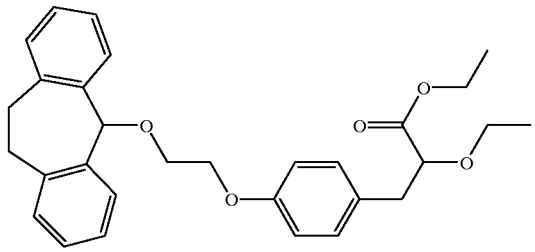

3-(4-[2-(10,11-Dihydro-5H-dibenzo[a,d]cyclohepten-5-yloxy)-ethoxy]-phenyl)-2-ethoxy-propanoic acid ethyl ester A mixture of 5-(3-mesyloxypropylidene)-10,11-dihydro-5H-dibenzo[a,d]cyclohepten (5.0 g, 15.2 mmol), ethyl 3-(4-hydroxyphenyl)-2-ethoxypropanoate (3.7 g, 15.5 mmol), potassium carbonate (2.9 g, 21 mmol) and dimethylformamide (10 ml) was heated at 100° C. for 5 h. Benzene (200 ml) and water (200 ml) were added and the phases were separated. The organic phase was dried and the solvent evaporated in vacuo. The residue was purified by chromatography on silica gel eluting with benzene/chloroform, to give first 2.5 g of 5-propenylidene-10,11-dihydro-5H-dibenzo (a,d)cyclohepten and then 1.5 g (21%) of the title compound as an oil. ¹H NMR (250 MHz, CDCl₃) δ7.10–7.35 (m, 10 H); 6.85 (d, 2 H); 6.06 (t, 1 H); 4.27 (q, 2 H); 4.07 (m, 3 H); 3.68 (m,₁ H); 3.45 (m, 1 H); 3.17 (bs, 4 H); 3.06 (d, 2 H); 2.69 (q, 2 H); 1.27 (t 3 H); 0.99 (t, 3 H).

EXAMPLE 9

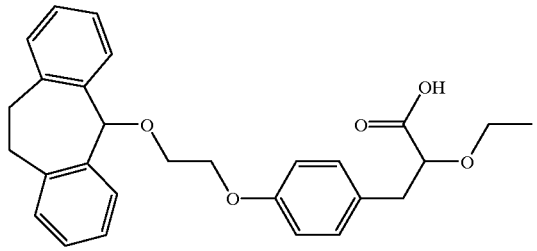

3-(4-[2-(10,11-Dihydro-5H-dibenzo[a,d]cyclohepten-5-yloxy)-ethoxy]-phenyl)-2-ethoxy-propanoic acid 3-(4-[2-(10,11-Dihydro-5H-dibenzo[a,d]cyclohepten-5-yloxy)-ethoxy]-phenyl)-2-ethoxy-propanoic acid ethyl ester (example 8) (1.5 g, 3.2 mmol) was dissolved in ethanol (30 ml) and 20% sodium hydroxide (3 ml) was added. After 3 days ethanol was evaporated in vacuo, water (50 ml) and hydrochloric acid (2 ml) were added and the mixture was extracted with dichloromethane. The organic phase was dried (MgSO₄) and the solvent evaporated in vacuo. The residue (1.1 g, 78%) was dissolved in ethanol and treated with (L)-lysine monohydrate (0.41 g). Ethanol was evaporated and the residue triturated with diethyl ether. The crystalline product was filtered off and dried in the air. This afforded 1.45 g of the title compound as salt with (L)-lysine (dihydrate). M.p. 148–150° C. ¹H NMR (250 MHz, DMSO-d₆ δ7.00–7.35 (m, 10 H); 6.75 (bd, J=8.2 Hz, 2 H); 6.26 (bs, 8 H); 5.91 (t, J=6.6 Hz, 1 H); 4.02 (t, J=6.2 Hz, 2 H); 3.76 (m, 1 H); 3.59 (m)+3.31 (m), 2 H; 3.07 (bs (4 H); 2.70–2,95 (m, 4 H); 2.51 (bq, 2 H); 1.66 (bm, 6 H); 1.03 (t, J=7.2 Hz, 3 H).

EXAMPLE 10

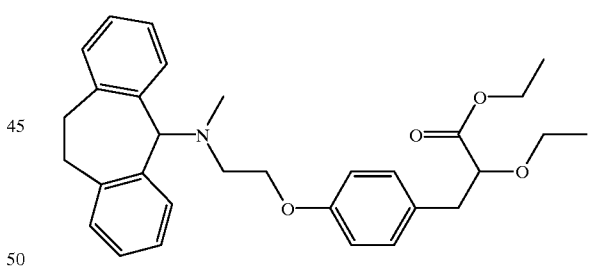

3-(4-[2-([10,11-dihydro-5H-dibenzo[a,d]cyclohepten-5-yl]-methyl-amino)-ethoxy]-phenyl)-2-ethoxypropanoic acid ethyl ester A mixture of 5-(methylamino)-10,11-dihydro-5H-dibenzo[a,d]cycloheptene hydrochloride(1.8 g, 6.94 mmol), ethyl 3-(4-bromethoxyphenyl)-2-ethoxypropanoate (2.4 g, 6.95 mmol), potassium carbonate (2.9 g, 21 mmol) and dimethylformamide (7 ml) was heated at 100° C. for 5 h. Benzene (200 ml) and water (200 ml) were added and the phases were separated. The organic phase was dried and the solvent evaporated in vacuo. The residue was purified by chromatography on silica gel eluting with benzene/chloroform to give 2.2 g (65%) of the title compound as an oil. RF=0.60 (chloroform/ethanol/ammonia=20:2:0.1)

EXAMPLE 11

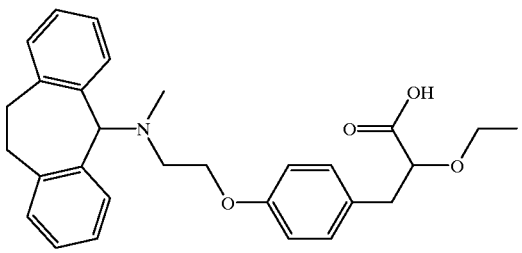

3-(4-[2-([10,11-dihydro-5H-dibenzo[a,d]cycloh epten-5-yl]-methyl-amino)-ethoxy]-phenyl)-2-ethoxypropanoic acid 3-(4-[2-([10,11-dihydro-5H-dibenzo[a,d]cyclohepten-5-yl]-methyl-amino)-ethoxy]-phenyl)-2-ethoxypropanoic acid ethyl ester (example 10)(1.5 g, 3.07 mmol) was dissolved in ethanol (20 ml) and 20% sodium hydroxide (2 ml) was added. After 6 days ethanol was evaporated in vacuo, water (50 ml) and acetic acid (2 ml) were added and the mixture was extracted with dichloromethane. The organic phase was dried (MgSO$_4$) and the solvent evaporated in vacuo. The residue (1.4 g) was dissolved in acetone and neutralized with solution of hydrogen chloride in diethyl ether. The solvents were evaporated and the residue was triturated with diethyl ether yielding 1.15 g (74%) of the title compound as amorphous solid (hemihydrate). $^1$H NMR (250 MHz, DMSO-d$_6$) δ10.50 (bs, 1 H); 7.60 (bs)+7.10–7.50 (m, 10 H), 6.87 (d, J=7.9 Hz, 2 H), 5.84 (bd, J=7.0 Hz, 1 H), 4.49 (bs, 2 H), 4.00 (t, J=5.6 Hz; +bm, 3 H), 3.30–3,60 (m+m, 4 H), 2.80–3.10 (s+bm, 7 H), 1.07 (t, J=7.2 Hz, 3 H).

EXAMPLE 12

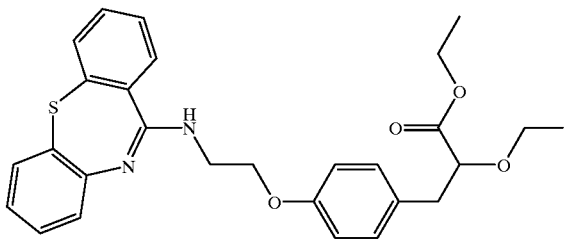

3-(4-[2-(Dibenzo[b,f]-1,4-thiazepin-11-ylamino)-ethoxy]-phenyl)-2-ethoxy-propionic acid ethyl ester A mixture of ethyl 3-(4-(2-bromethoxy)phenyl)-2-ethoxypropanoate (3.05 g, 8.8 mmol), potassium phtalimide (2.0 g, 10.8 mmol) and dimethylformamide (20 ml) was heated to 100° C. for 16 h, benzene (200 ml) and water (200 ml) were added and the phases were separated. The organic phase was dried and the solvent evaporated in vacuo. The residue was dissolved in ethanol (60 mL), hydrazine hydrate (1.3 ml) was added and the mixture was refluxed for 2 h, filtered and the solvent evaporated to give 2.4 g (96%) of ethyl 3-(4-(2-aminoethoxy) phenyl)-2-ethoxypropanoate as an oil. Hydrogen oxalate hemihydrate was prepared for characterization by neutralization with oxalic acid in acetone. M.p. 146–148° C. A mixture of dibenzo[b,f9-1,4-thiazepin-11(10H)-thione (2.20 g, 9 mmol; prepared as described in Coll.Czech.Chem.Commun. 48, 1465 (1983), 3-(4-(2-aminoethoxy)phenyl)-2-ethoxypropanoic acid ethyl ester (2.60 g, 8.9 mmol) and 3-methyl-1-butanol (70 ml) was stirred and heated at 150° C. for 16 h. The solvent was evaporated in vacuo, dichloromethane (50 ml) and water (50 ml) were added, the mixture was filtered and the phases were separated. The organic phase was dried (MgSO$_4$) and the solvent was evaporated in vacuo to give a residue which was purified by column chromatography on silica gel eluting with chloroform. This afforded 0.7 g of the starting thione and then 1.7 g (38%) of the title compound as an oil. $^1$H NMR (250 MHz, CDCl$_3$) δ7.05–7.50 (m, 9 H), 6.85–6.95 (m, 3 H), 5.15 (bs, 1 H), 4.25 (m, 2 H), 4.16 (q, J=7.2 Hz, 2 H), 3.96 (t+m, 3 H), 3.59 (m, 1 H), 3.34 (m, 1 H), 2.95 (d, J=6.4 Hz, 2 H), 1.22 (t, J=7.2 Hz, 3 H), 1.16 (t, J=7.2 Hz, 3 H).

EXAMPLE 13

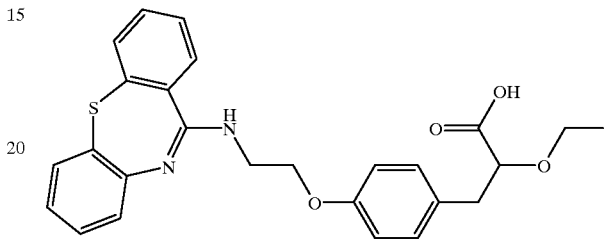

3-(4-[2-(Dibenzo[b,f]-1,4-thiazepin-11-ylamino)-ethoxy]-phenyl)-2-ethoxy-propionic acid 3-(4-[2-(Dibenzo[b,f]-1,4-thiazepin-11-ylamino)-ethoxy]-phenyl)-2-ethoxy-propanoic acid ethyl ester (1.6 g, 3.26 mmol) was dissolved in ethanol (30 ml) and 20% sodium hydroxide (3 ml) was added. After 6 days ethanol was evaporated in vacuo, water (50 ml) and acetic acid (3 ml) were added, the product was filtered off and dried yielding 1.4 g (87%) of the title compound as hydrate. $^1$H NMR (250 MHz, DMSO-d6) δ7.3–7.6 (m, 6 H), 7.10–7.25 (m, 3 H), 6.82–7.15 (m+bs, 4–5 H), 4.26 (bt, J=4.9 Hz, 2 H), 3.88 (dd, J=7.6 Hz and 4.2 Hz, 1 H), 3.78 (bs, 2 H), 3.54 (m)+3.25 (m), 2 H; 2.91 (bdd, 1 H), 2.70–2.82 (m, 1 H), 1.03 (t, J=7.2 Hz, 3 H).

What is claimed is:
1. A compound of formula (Ia)

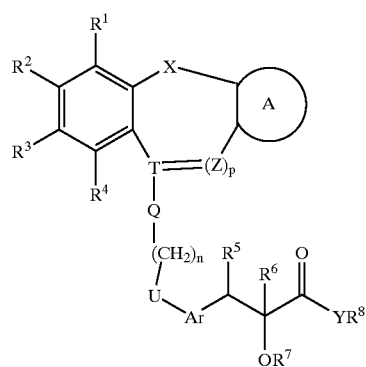

(Ia)

wherein $R^1$, $R^2$, $R^3$, and $R^4$ independently of each other represent hydrogen, halogen, perhalomethyl, hydroxy, nitro, cyano, formyl, or $C_{1-12}$alkyl, $C_{4-12}$-alkenynyl, $C_{2-12}$-alkenyl, $C_{2-12}$-alkynyl, $C_{1-12}$alkoxy, phenyl, naphthyl, acyl, acyloxy, hydroxyC$_{1-12}$alkyl, amino, acylamino, $C_{1-12}$alkylamino, arylamino, aralkylamino, aminoC$_{1-12}$alkyl, $C_{1-12}$alkoxycarbonyl, aryloxycarbonyl, aralkoxycarbonyl, $C_{1-12}$alkoxyC$_{1-12}$alkyl, aryloxyC$_{1-12}$alkyl, aralkoxyC$_{1-12}$alkyl, $C_{1-12}$alkylthio, thioC$_{1-12}$alkyl, $C_{1-12}$alkoxycarbonylamino, aryloxycarbonylamino, aralkoxycarbonylamino, —$COR^{11}$, or —$SO_2R^{12}$, wherein $R^{11}$ and $R^{12}$ independently of each other are selected from hydroxy, halogen, perhalomethyl, $C_{1-6}$alkoxy or amino optionally substituted with one or more $C_{1-6}$alkyl, perhalomethyl phenyl or naphthyl; optionally substituted with one or more halogen, perhalomethyl, hydroxy, nitro or cyano;

or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl;

ring A is phenyl optionally substituted with one or more halogen, perhalomethyl, hydroxy, nitro or cyano;

X is —O—(CHR$^9$)—, —S—(CHR$^9$)—, —$CH_2$—(SO)—, or —$CH_2$—($SO_2$)—, wherein $R^9$ is hydrogen, halogen, hydroxy, nitro, cyano, formyl, $C_{1-12}$alkyl, $C_{1-12}$alkoxy, phenyl, naphthyl, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —$COR^{13}$, or —$SO_2R^{14}$, wherein $R^{13}$ and $R^{14}$ independently of each other are selected from hydroxy, halogen, $C_{1-6}$alkoxy, amino optionally substituted with one or more $C_{1-6}$alkyl, perhalomethyl phenyl or naphthyl;

T is >CH— or >C<;

Z is —$CH_2$—, =CH—, >N—, —O—, —S—, >CO, >SO, >$SO_2$, >$NR^{15}$, wherein $R^{15}$ is hydrogen, halogen, hydroxy, nitro, cyano, formyl, $C_{1-12}$alkyl, $C_{1-12}$alkoxy, phenyl, naphthyl, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —$COR^{16}$, or —$SO_2R^{17}$, wherein $R^{16}$ and $R^{17}$ independently of each other are selected from hydroxy, halogen, $C_{1-6}$alkoxy, amino optionally substituted with one or more $C_{1-6}$alkyl, perhalomethyl phenyl or naphthyl;

Q is —O—, —S—, >$NR^{18}$, wherein $R^{18}$ is hydrogen, halogen, hydroxy, nitro, cyano, formyl, $C_{1-12}$alkyl, $C_{1-12}$alkoxy, phenyl, naphthyl, acyl, acyloxy, hydroxyalkyl, amino, acylamino, $C_{1-12}$alkyl-amino, arylamino, aralkylamino, amino$C_{1-12}$alkyl, $C_{1-12}$alkoxycarbonyl, aryloxycarbonyl, aralkoxycarbonyl, $C_{1-12}$alkoxy$C_{1-12}$alkyl, aryloxy$C_{1-12}$alkyl, aralkoxy$C_{1-12}$alkyl, $C_{1-12}$alkylthio, thio$C_{1-12}$alkyl, $C_{1-12}$alkoxycarbonylamino, aryloxycarbonylamino, aralkoxycarbonylamino, —$COR^{19}$, or —$SO_2R^{20}$, wherein $R^{19}$ and $R^{20}$ independently of each other are selected from hydroxy, halogen, $C_{1-6}$alkoxy, amino optionally substituted with one or more $C_{1-6}$alkyl, perhalomethyl, phenyl or naphthyl, U is —O—, —S—, >$SO_2$, >$NR^{21}$, wherein $R^{21}$ is hydrogen or $C_{1-6}$alkyl;

T===(Z)$_p$ represents a single bond or a double bond;

Ar represents arylene, selected from the group consisting of phenylene, napthylene, optionally substituted with halogen, amino, hydroxy, $C_{1-6}$-alkyl or $C_{1-6}$-alkoxy, phenyl or naphthyl; heteroarylene, selected from furan, thiophene, pyrrole, imidaxole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indol, benzimidazole, benzofuran, pteridine and purine, or a divalent heterocyclic group selected from pyrrolidine, pyrroline, pyrazoline, pyrazolidine, 1,2-oxathiolane, imidazolidine, imidazoline, 4-oxazolone, tetrahydrofurazan, tetrazole, piperidine, piperazine, morpholine, triazine, trioxane, trithiane, tetrazine, tetraoxane and tetrathiane, said heterocyclic group .optionally substituted with one or more $C_{1-6}$alkyl, or axyl,said aryl selected from the group consisting of phenyl, naphtyl optionally substituted with halogen, amino, hydroxy, $C_{1-6}$-alkyl or $C_{1-6}$-alkoxy;

$R^5$ represents hydrogen, hydroxy, halogen, $C_{1-12}$alkoxy, $C_{1-12}$alkyl, $C_{4-12}$-alkenynyl, $C_{2-12}$-alkenyl or $C_{2-12}$-alkynyl; optionally substituted with one or more halogen, perhalomethyl, hydroxy, nitro or cyano; or $R^5$ forms a bond together with $R^6$;

$R^6$ represents hydrogen, hydroxy, halogen, $C_{1-12}$alkoxy, $C_{1-12}$alkyl, $C_{4-12}$-alkenynyl, $C_{2-12}$-alkenyl, $C_{2-12}$-alkynyl or acyl; optionally substituted with one or more halogen, perhalomethyl, hydroxy, nitro or cyano; or $R^6$ forms a bond together with $R^5$;

$R^7$ represents hydrogen, $C_{1-12}$alkyl, $C_{4-12}$-alkenynyl, $C_{2-12}$-alkenyl, $C_{2-12}$-alkynyl, phenyl, naphthyl, $C_{1-12}$alkoxy$C_{1-12}$alkyl, $C_{1-12}$alkoxycarbonyl, aryloxycarbonyl, $C_{1-12}$alkylaminocarbonyl, arylaminocarbonyl, or acyl; optionally substituted with one or more halogen, perhalomethyl, hydroxy, nitro or cyano;

$R^8$ represents hydrogen, $C_{1-12}$alkyl, $C_{4-12}$-alkenynyl, $C_{2-12}$-alkenyl, $C_{2-12}$-alkynyl, phenyl or naphthyl; optionally substituted with one or more halogen, perhalomethyl, hydroxy, nitro or cyano;

Y represents oxygen, sulphur or $NR^{10}$, where $R^{10}$ represents hydrogen, $C_{1-12}$alkyl, phenyl, naphthyl, hydroxy$C_{1-12}$alkyl or when Y is $NR^{10}$, $R^8$ and $R^{10}$ may form a 5 or 6 membered nitrogen containing ring, optionally substituted with one or more $C_{1-6}$alkyl;

n is an integer ranging from 1 to 4;

p is 0;

or a pharmaceutically acceptable salt thereof.

2. A compound of claim 1 wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, phenyl, naphthyl, acyl, acyloxy, hydroxy$C_{1-7}$alkyl, amino, acylamino, $C_{1-7}$alkyl-amino, arylamino, aralkylamino, amino$C_{1-7}$alkyl, $C_{1-7}$alkoxycarbonyl, aryloxycarbonyl, aralkoxycarbonyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino, aralkoxycarbonylamino, —$COR^{11}$, or —$SO^2R^{12}$, wherein $R^{11}$ and $R^{12}$ independently of each other are selected from hydroxy, perhalomethyl, $C_{1-6}$alkoxy or amino optionally substituted with one or more $C_{1-6}$alkyl, perhalomethyl, phenyl or naphthyl; optionally substituted with one or more halogen, perhalomethyl, hydroxy, nitro or cyano;

or $R^1$ and $R^2$, $R^2$ and $R^3$ and/or $R^3$ and $R^4$ may form a cyclic ring containing from 5 to 7 carbon atoms optionally substituted with one or more $C_{1-6}$alkyl.

3. A compound of claim 1 wherein $R^1$, $R^2$, $R^3$, and $R^4$ independently of each other represent hydrogen, halogen, perhalomethyl, hydroxy, cyano, or $C_{1-7}$alkyl, $C_{4-7}$- alkenynyl, $C_{2-7}$-alkenyl, $C_{2-7}$-alkynyl, $C_{1-7}$alkoxy, phenyl, naphthyl, acyl, hydroxy$C_{1-7}$alkyl, amino, acylamino, $C_{1-7}$alkyl-amino, arylamino, aralkylamino, amino$C_{1-7}$alkyl, $C_{1-7}$alkoxy$C_{1-7}$alkyl, aryloxy$C_{1-7}$alkyl, aralkoxy$C_{1-7}$alkyl, $C_{1-7}$alkylthio, thio$C_{1-7}$alkyl, $C_{1-7}$alkoxycarbonylamino, aryloxycarbonylamino or aralkoxycarbonylamino.

4. A compound of claim 1 wherein $R^1$, $R^2$, $R^3$, and $R^4$ independently of each other represent hydrogen, halogen, perhalomethyl, hydroxy, cyano, or $C_{1-7}$alkyl, $C_{4-7}$-alkenynyl, $C_{2-7}$-alkenyl, $C_{2-7}$-alkynyl, $C_{1-7}$alkoxy, phenyl, naphthyl, acyl, hydroxy$C_{1-7}$alkyl, amino, $C_{1-7}$alkyl-amino, arylamino, aralkylamino, $C_{1-7}$alkoxy$C_{1-7}$alkyl, aryloxy$C_{1-7}$alkyl, aralkoxy$C_{1-7}$alky or $C_{1-7}$alkylthio.

5. A compound of claim 1 wherein $R^1$, $R^2$, $R^3$, and $R^4$ independently of each other represent hydrogen, halogen, perhalomethyl, or $C_{1-7}$alkyl, $C_{4-7}$-alkenynyl, $C_{2-7}$-alkenyl, $C_{2-7}$-alkynyl, phenyl, naphthyl, hydroxy$C_{1-7}$alkyl, $C_{1-7}$alkoxy$C_{1-7}$alkyl, aryloxy$C_{1-7}$alkyl or aralkoxy$C_{1-7}$alkyl.

6. A compound of claim 1 wherein $R^1$, $R^2$, $R^3$, and $R^4$ independently of each other represent hydrogen, halogen or $C_{1-7}$alkyl.

7. A compound of claim 1 wherein $R^1$, $R^2$, $R^3$, and $R^4$ represent hydrogen.

8. A compound of claim 1 wherein X is —O—(CHR$^9$)— or —S—(CHR$^9$)—, wherein $R^9$ is hydrogen.

9. A compound of claim 1 wherein T is >C<.

10. A compound of claim 1 wherein Q is —O—, —S—, >NR$^{18}$, wherein $R^{18}$ is hydrogen or $C_{1-7}$alkyl.

11. A compound of claim 1 wherein Q is >NR$^{18}$, wherein $R^{18}$ is hydrogen.

12. A compound of claim 1 wherein U is —O—.

13. A compound of claim 1 wherein Ar represents arylene optionally substituted with one or more $C_{1-6}$alkyl, phenyl or naphthyl.

14. A compound of claim 1 wherein Ar is phenyl.

15. A compound of claim 1 wherein $R^5$ represents hydrogen, hydroxy, halogen, $C_{1-7}$alkoxy, $C_{1-7}$alkyl, $C_{4-7}$-alkenynyl, $C_{2-7}$-alkenyl, $C_{2-7}$-alkynyl or $R^5$ forms a bond together with $R^6$.

16. A compound of claim 1 wherein $R^5$ represents hydrogen or $R^5$ forms a bond together with $R^6$.

17. A compound of claim 1 wherein $R^6$ represents hydrogen, hydroxy, halogen, $C_{1-7}$alkoxy, $C_{1-7}$alkyl, $C_{4-7}$-alkenynyl, $C_{2-7}$-alkenyl, $C_{2-7}$-alkynyl, or $R^6$ forms a bond together with $R^5$.

18. A compound of claim 1 wherein $R^6$ represents hydrogen or $R^6$ forms a bond together with $R^5$.

19. A compound of claim 1 wherein $R^7$ represents hydrogen, $C_{1-7}$alkyl, $C_{4-7}$-alkenynyl, $C_{2-7}$-alkenyl, $C_{2-7}$-alkynyl, $C_{1-7}$alkoxy$C_{1-7}$alkyl, $C_{1-7}$alkoxycarbonyl, aryloxycarbonyl, $C_{1-7}$alkylaminocarbonyl, arylaminocarbonyl or acyl.

20. A compound of claim 1 wherein $R^7$ represents hydrogen, $C_{1-7}$alkyl, $C_{4-7}$-alkenynyl, $C_{2-7}$-alkenyl or $C_{2-7}$-alkynyl.

21. A compound of claim 1 wherein $R^7$ is $C_{1-12}$alkyl.

22. A compound of claim 1 wherein $R^8$ represents hydrogen, $C_{1-7}$alkyl, $C_{4-7}$-alkenynyl, $C_{2-7}$-alkenyl or $C_{2-7}$-alkynyl; optionally substituted with one or more halogen, perhalomethyl, hydroxy, nitro or cyano.

23. A compound of claim 1 wherein $R^5$ represents hydrogen, $C_{1-7}$alkyl, $C_{4-7}$-alkenynyl, $C_{2-7}$-alkenyl, $C_{2-7}$-alkynyl phenyl or naphthyl.

24. A compound of claim 1 wherein $R^8$ is hydrogen or $C_{1-12}$alkyl.

25. A compound of claim 1 wherein Y represents oxygen, sulphur or NR$^{10}$, where $R^{10}$ represents hydrogen, $C_{1-7}$alkyl, phenyl, naphthyl or hydroxy$C_{1-7}$alkyl groups.

26. A compound of claim 1 wherein Y is oxygen.

27. A compound of claim 1 wherein n is an integer ranging from 2 to 3.

28. A compound of claim 1 wherein T is >CH—.

29. A compound of claim 1 wherein T is >C<.

30. A compound of claim 1 wherein Q is —O—.

31. A compound of claim 1 wherein Q is —S—.

32. A compound of claim 1 wherein Q is >NR$^{18}$, wherein $R^{18}$ is H.

33. A compound of claim 1 wherein n is 2.

34. A compound of claim 1 wherein U is —O—.

35. A compound of claim 1 wherein Ar is phenylene.

36. A compound of claim 1 wherein $R^5$ is H.

37. A compound of claim 1 wherein $R^6$ is H.

38. A compound of claim 1 wherein $R^7$ is ethyl.

39. A compound of claim 1 wherein $R^8$ is H.

40. A compound of claim 1 wherein X is —O—(CHR$^9$)—, wherein $R^9$ is H.

41. A compound of claim 1 wherein X is —S—(CHR$^9$)—, wherein $R^9$ is H.

42. A compound of claim 1 which is:
3-(4-[2-(6,11-Dihydrodibenzo[b,e]thiepin-11-yloxy)-ethoxy]-phenyl)-2-ethoxy-propionic acid ethyl ester,
3-(4-[2-(6,11-Dihydrodibenzo[b,e]thiepin-11-yloxy)-ethoxy]-phenyl)-2-ethoxy-propionic acid,
or
3-(4-[2-(6,11-Dihydrodibenzo[b,e]oxepin-11-yloxy)-ethoxy]-phenyl)-2-ethoxy-propionic acid ethyl ester,
or a pharmaceutically acceptable salt thereof.

43. A pharmaceutical composition comprising, as an active ingredient, an effective amount of a compound of claim 1 together with a pharmaceutically acceptable carrier or diluent.

44. The composition of claim 43 in unit dosage form, comprising from about 0.05 to about 100 mg of the compound.

45. The pharmaceutical composition of claim 43 wherein the route of administration is oral, nasal, transdermal, pulmonal, or parenteral.

46. A method of treating diabetes or obesity, the method comprising administering to a subject in need thereof an effective amount of a compound of claim 1.

47. The method of claim 46, wherein the effective amount of the compound is in the range of from about 0.05 to about 100 mg per day.

48. A compound of claim 1 wherein Ar is a heteroaryl group selected from furan, thiophenepyrrole, imidaxole, pyrazole, triazole, pyridine, pyrazine, pyrimidine, pyridazine, isothiazole, isoxazole, oxazole, oxadiazole, thiadiazole, quinoline, isoquinoline, quinazoline, quinoxaline, indol, benzimidazole, benzofuran, pteridine and purine.

49. A compound of claim 1 wherein Ar is a divalent heterocyclic group selected from pyrrolidine, pyrroline, pyrazoline, pyrazolidine, 1,2-oxathiolane, imidazolidine, imidazoline, 4-oxazolone, tetrahydrofurazan, tetrazole, piperidine, piperazine, morpholine, triazine, trioxane, trithiane, tetrazine, tetraoxane and tetrathiane.

* * * * *

UNITED STATES PATENT AND TRADEMARK OFFICE
CERTIFICATE OF CORRECTION

PATENT NO. : 6,525,086 B2
DATED : February 25, 2003
INVENTOR(S) : Jeppesen et al.

It is certified that error appears in the above-identified patent and that said Letters Patent is hereby corrected as shown below:

Column 34,
Line 50, "T-Z" the double line connecting T to Z should be dashed -- T= =Z --

Column 36,
Line 1, "thiophene,pyrrole" should read -- thiophenepyrrole --.
Lines 12 and 13, "$C_{1-6}$alkyl, or axyl" should read -- $C_{1-6}$alkyl, or aryl --.

Signed and Sealed this

Twenty-fifth Day of May, 2004

JON W. DUDAS
*Acting Director of the United States Patent and Trademark Office*